(12) United States Patent
Yoshida et al.

(10) Patent No.: US 10,271,828 B2
(45) Date of Patent: Apr. 30, 2019

(54) IMAGE FILE CREATION METHOD, MEDIUM WITH IMAGE FILE CREATION PROGRAM RECORDED AND IMAGE FILE CREATION APPARATUS

(71) Applicant: OLYMPUS CORPORATION, Hachioji-shi, Tokyo (JP)

(72) Inventors: Hideaki Yoshida, Hachioji (JP); Masayasu Chida, Lexington, MA (US); Ryo Koshida, Fuchu (JP); Yasunori Makara, Hino (JP); Osamu Ono, Hidaka (JP); Osamu Nonaka, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 84 days.

(21) Appl. No.: 15/593,384

(22) Filed: May 12, 2017

(65) Prior Publication Data

US 2017/0337683 A1  Nov. 23, 2017

(30) Foreign Application Priority Data

May 18, 2016   (JP) .................................. 2016-099751

(51) Int. Cl.
*A61B 10/02*    (2006.01)
*G06F 19/00*    (2018.01)
*A61B 10/06*    (2006.01)

(52) U.S. Cl.
CPC .......... *A61B 10/0283* (2013.01); *A61B 10/06* (2013.01); *G06F 19/00* (2013.01); *G06F 19/321* (2013.01)

(58) Field of Classification Search
CPC ..... A61B 10/0283; A61B 10/06; G06F 19/00; G06F 19/321; G06T 2207/30024; G06T 2207/30196; G06T 7/0012
See application file for complete search history.

(56) References Cited

U.S. PATENT DOCUMENTS

2004/0249291 A1* 12/2004 Honda ............... A61B 1/00009
                                              600/476
2005/0272971 A1   12/2005 Ohnishi
2009/0131746 A1*  5/2009 Seo ..................... A61B 1/00045
                                              600/101

(Continued)

FOREIGN PATENT DOCUMENTS

CN   1678234 A      10/2005
JP   09-281108 A    10/1997
JP   2007-175430 A   7/2007

OTHER PUBLICATIONS

Office Action issued in corresponding Chinese Patent Application No. 201710347117.0 dated Oct. 8, 2018, consisting of 5 pp.

*Primary Examiner* — Manuchehr Rahmjoo
(74) *Attorney, Agent, or Firm* — Volpe and Koenig, P.C.

(57) ABSTRACT

A image file creation method includes: an image pickup step of picking up an image of a living body; a treatment detection step of detecting a treatment related to the living body; and an image file creation step of creating, according to a result of the detection in the treatment detection step, an image file, for image data obtained in the image pickup step, with specimen information including information indicating that the image is an image relating to specimen collection by the treatment related to the living body, to record data of, e.g., an image of a tissue such as a cell itself and data of, e.g., an image related to the tissue such as the cell, a treatment and/or collection, enabling a plurality of institutions, facilities, etc., to easily refer to information on the tissue such as the cell.

13 Claims, 11 Drawing Sheets

(56) References Cited

U.S. PATENT DOCUMENTS

2014/0303435 A1* 10/2014 Taniguchi .......... A61B 1/00009
  600/103
2016/0253456 A1* 9/2016 Goede .................. G06F 19/321
  705/3

* cited by examiner

IMAGE FILE CREATION METHOD, MEDIUM WITH IMAGE FILE CREATION PROGRAM RECORDED AND IMAGE FILE CREATION APPARATUS

CROSS REFERENCE TO RELATED APPLICATION

This application claim is benefit of Japanese Application No. 2016-099751 in Japan on May 18, 2016, the contents of which are incorporated by this reference.

BACKGROUND OF THE INVENTION

1. Field of the Invention

The present invention relates to an image file creation method, a medium with an image file creation program recorded and an image file creation apparatus, the method, the program and the apparatus reliably and efficiently assisting work.

2. Description of the Related Art

In recent years, medical image devices such as endoscopes have been growing in image quality, enabling a tissue to be clearly viewed and enhancing reliability of surgery, treatment and examination.

Obtained medical images are recorded for various uses. In this case, it is necessary to manage the histories of the recorded images. Therefore, when, e.g., an examination, a treatment, a remedy or the like is performed and a medical image is recorded, a patient subjected to, e.g., the examination and the medical image are recorded in association with each other.

For example, display of a patient ID for identifying a patient using, e.g., a patient registration card issued by a medical institution or medical insurance information may be superimposed on a medical image to record the medical image with the patient ID superimposed. Also, for example, a medical image and information such as a patient ID may be recorded in association with each other.

As stated above, a patient subjected to an examination and a medical image relating to the patient are recorded in association with each other to make it easy to know which patient the recorded medical image belongs to.

Also, in some cases, a tissue in a body is extracted using, e.g., an endoscope or a skin tissue is collected and an examination, such as a biopsy or a blood examination, of the tissue is performed in, e.g., a facility other than a medical setting. A specimen obtained in the biopsy is sent to an examination institution or facility, and a microscopic examination or a further examination, e.g., using a reagent is performed in the examination institution or the like. Note that Japanese Patent Application Laid-Open Publication No. 9-281108 discloses an apparatus that displays information on a specimen on a display together with an observation image.

SUMMARY OF THE INVENTION

An image file creation method according to an aspect of the present invention includes: an image pickup step of picking up an image of a living body; a treatment detection step of detecting a treatment related to the living body; and an image file creation step of creating, according to a result of the detection in the treatment detection step, an image file provided, for image data obtained in the image pickup step, with specimen information including information indicating that the image is an image relating to specimen collection by the treatment related to the living body.

Also, a medium with an image file creation program according to an aspect of the present invention recorded, the image file creation program causing a computer to perform: an image pickup step of picking up an image of a living body; a treatment detection step of detecting a treatment related to the living body; and an image file creation step of creating, according to a result of the detection in the treatment detection step, an image file provided, for image data obtained in the image pickup step, with specimen information including information indicating that the image is an image relating to specimen collection by the treatment related to the living body.

Also, an image file creation apparatus according to an aspect of the present invention includes: an image pickup section configured to pick up an image of a living body; a treatment detection section configured to detect a treatment related to the living body; and an image file creation section configured to create, according to a result of the detection by the treatment detection section, an image file provided, for image data obtained by the image pickup section, with specimen information including information indicating that the image is an image relating to specimen collection by the treatment related to the living body.

The above and other objects, features and advantages of the invention will become more clearly understood from the following description referring to the accompanying drawings.

DETAILED DESCRIPTION OF THE PREFERRED EMBODIMENT

Figure 1:
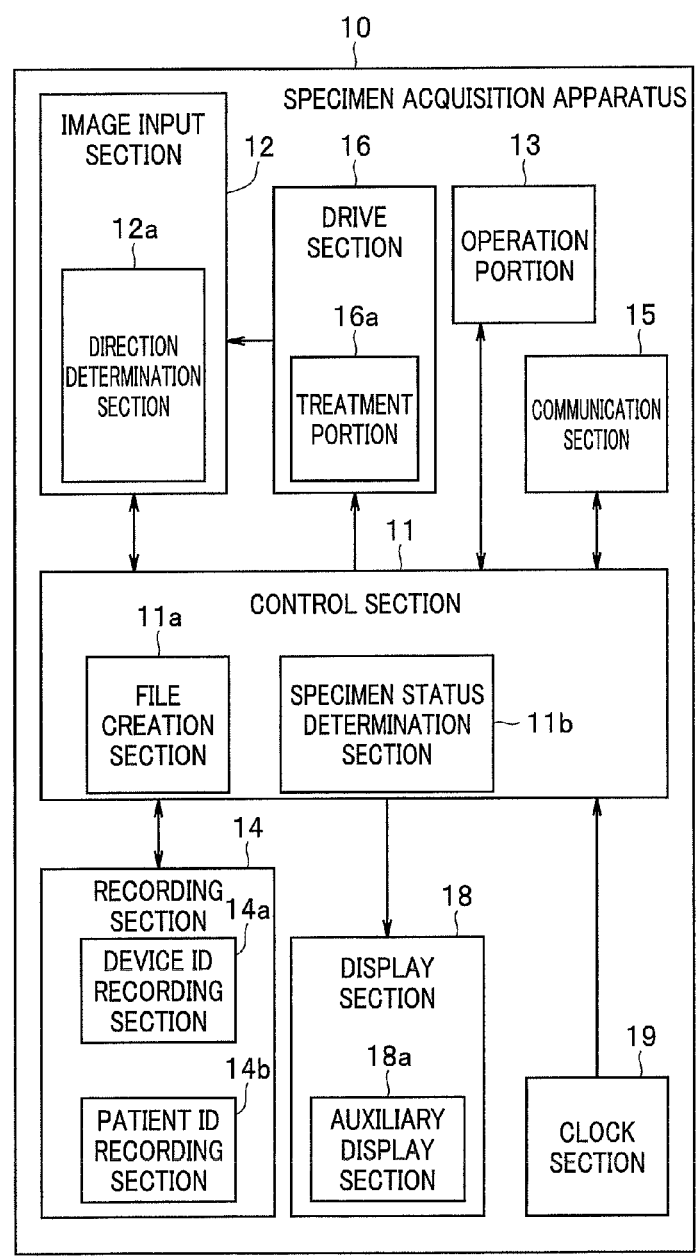
FIG. 1 is a block diagram illustrating a medical system in which an image file creation method according to an embodiment of the present invention is implemented.

An embodiment of the present invention will be described below with reference to the drawings.

FIGS. 1 to 4 are block diagrams illustrating a medical system in which an image file creation method according to an embodiment of the present invention is implemented.

The present embodiment is intended to assist bio-related confirmation or processing in a plurality of medical institutions, etc., that deal with cells and images relating to cells or tissues. Examples of the plurality of medical institutions, etc., include not only a medical institution such as a hospital that acquires or collect a tissue or cells by means of, e.g., a biopsy (hereinafter, treatment or work for extracting a part of, e.g., a diseased part from, e.g., a living body via, e.g., an instrument for further examination of the part via a microscope or another method is referred to as "biopsy") or implant processed cells, but also a management institution with a management system incorporated, the management system managing images picked up and recorded at the time of acquisition of cells, an examination institution that, e.g., examines, observes or cultivate a tissue or cells of, e.g., a specimen (hereinafter, what is called clinical specimen which is an examination object such as a part of a tissue or cells obtained from, e.g., a diseased part being subjected to component analysis in various ways or being subjected to an examination to determine, e.g., whether or not microorganisms and others are present in, e.g., the aforementioned biopsy is referred to as "specimen") and a research institution or the like that conducts a research on cells. It should be understood that an object (collected object) at the time of extraction is not limited to a tissue or cells of a living body, and an object to be further examined after extraction is not only a specimen and may be an extracted foreign object, components or others. In other words, it is important that an image at the time of collection and an image of an extracted object further subjected to, e.g., an examination, observation or processing are easily associated with each other.

In the present embodiment, a network is built among a plurality of medical institutions, etc., and images relating to tissues or cells are subjected to centralized data management to enable use of the images subjected to centralized data management in the respective medical institutions, etc. Consequently, in the respective medical institutions, etc., bio-related examination, treatment, work, processing, etc., can efficiently be assisted, making it easy to ensure, for example, management of specimens in examinations and searchability of the specimens and reliability and safety of the examinations. Furthermore, attention is being drawn to applications such as cultivating an obtained tissue to utilize the tissue for regenerative medicine or utilize the tissue for development, testing, etc., of drugs, and thus it is very important to be able to manage a history of a collected object at the time of collection.

A bio-related apparatus in the present embodiment is an apparatus to be used in a medical institution or the like, and examples of the bio-related apparatus include not only an apparatus used in, e.g., an examination by, e.g., an clinician that performs a medical action, but also an apparatus such as a server included in a management system that manages cells and images obtained as a result of a medical action and an examination apparatus in an examination institution that examines acquired cells. Also, for example, if collected objects such as cells are processed and/or examined in, e.g., an examination institution or a research institution, various apparatuses in such examination institution or research institution or the like fall under the bio-related apparatus. In other words, in the present embodiment, processing relating to a tissue, cells or the like and processing for recording, managing and reproducing an image (medical image) of the tissue, cells, etc. at the time of the processing are each referred to as "bio-related processing", and an apparatus that performs bio-related processing is referred to as "bio-related apparatus". In the present embodiment, it is desirable that bio-related apparatuses installed in, e.g., medical institutions can mutually give and receive information via a network such as a dedicated facility linkage or the Internet.

Note that with reference to FIGS. 1 to 4, for example, as bio-related apparatuses, a specimen acquisition apparatus that performs a biopsy of a patient, which is operated by, e.g., a clinician, an image management apparatus included in a management system that manages medical images acquired by a clinician, an information terminal that can edit image files managed by the image management apparatus and an examination apparatus in an examination institution that examines a specimen acquired by a clinician will be described as examples. The bio-related apparatuses in FIG. 1 to FIG. 4 may be provided in, e.g., one medical institution or may be disposed in, e.g., a plurality of different medical institutions.

FIG. 1 is a block diagram illustrating a specimen acquisition apparatus 10, which is a bio-related apparatus. The specimen acquisition apparatus 10 in FIG. 1 is, for example, an apparatus to be operated by a clinician in a hospital. For the specimen acquisition apparatus 10 in FIG. 1, not only a treatment instrument configured to collect a specimen such as a needle, tweezers or a surgical knife, but also, in the case of the inside of a body, an endoscope system or a special scope system and a treatment instrument related, attached or linked to the endoscope system or the special scope system, the treatment instrument enabling collection of a specimen, may be employed.

In recent years, a tissue is collected by making the tissue adhere to a material having viscosity. Use of such apparatus and/or instrument and dedicated products such as supplies for, e.g., a living body is generally referred to as "treatment". In other words, use of such apparatus and/or treatment instrument can be detected using, e.g., ID information each device has, using results of feature determination for images of the apparatus and/or the treatment instrument or determination of character data in a seal attached to the product or an image pattern signal. Also, what treatment was performed can be determined by detection and analysis of a name or an abbreviated name based on, e.g., a voice. These approaches may be both used, and a timing at which a sample such as a collected object was acquired from a living body may be determined according to a time at which a particular condition is met.

A specimen acquisition apparatus 10, which serves as an apparatus that acquires cells or collects a tissue, includes a drive section 16. The drive section 16 includes a treatment portion 16a, and the treatment portion 16a can acquire cells in a subject. For example, the treatment portion 16a can include a treatment instrument such as bio forceps inserted in a treatment instrument channel in an insertion portion of an endoscope. The drive section 16 may include a non-illustrated drive mechanism configured to drive the treatment portion 16a such as forceps. The driving is performed by an actuator, or is caused by human power such as grasping power of an operator being distantly transmitted and exerted. Also, the drive section 16 may drive a mechanism configured to suck an acquired object.

The specimen acquisition apparatus 10 includes an image input section 12. The image input section 12 can acquire a picked-up image of a subject. In particular, the image input section 12 can acquire an image of a subject at the time of acquisition of a tissue such as cells or a collected object of the subject via the treatment portion 16a (hereinafter referred to as "image at the time of cell acquisition"). For example, the image input section 12 includes an optical system for image pickup and an image pickup device, and can acquire a movie or a still image shot of acquisition of a tissue such as cells or a collected object by the treatment portion 16a as an image at the time of cell acquisition. Although it has been described that the specimen acquisition apparatus 10 includes the image input section 12, the specimen acquisition apparatus 10 and the image input section 12 may be separate from each other as long as linked control is obtained.

The image input section 12 may include, for example, an image pickup section using an image pickup device such as a CMOS sensor or a CCD sensor provided at a distal end of an insertion portion of a non-illustrated endoscope or in the case of an endoscope, may include one configured to acquire an image guided by, e.g., a dedicated optical system via an image pickup device even if the one is not provided at the distal end, and the image pickup section may be substituted by an image pickup section attached to a dedicated scope other than an endoscope or a wearable image pickup section worn by a person who performs a treatment or an assistant. Also, the image input section 12 may acquire an image resulting from imaging a result of emission and collection of ultrasound. The image input section 12 may be capable of picking up an image of the treatment portion 16a acquiring a tissue, cells or the like inside a subject in which the insertion portion of the endoscope is inserted and output data of the picked-up image to a control section 11. Although the image input section 12 needs to be linked with the specimen acquisition apparatus 10, for example, if a doctor or the like puts a device such as a wearable camera on, e.g., his/her head portion, the device serves as the image input section. In other words, an image indicating a collection status at the time of collection, the collection status being equivalent to a status viewed by a doctor, a dentist or an examiner at the time of collection of an object to be examined, from the skin, the inside of the oral cavity or the inside of an ear, a nose, and a throat can be obtained. This image enables recording a collected object acquisition state while a doctor devoting himself/herself to the treatment or the like without being distracted by troublesome recording work. Since the image includes different pieces of information, these pieces of image information are analyzed or associated with pieces of time information, enabling determination of the content and details of the treatment. Depending on the specialty of the apparatus and/or the treatment instrument that is being used, determination of, e.g., which part of a living body has been collected as an object to be examined can be made. For example, a magnetic coil employed in a known endoscope insertion shape observation apparatus or a three-dimensional shape model image of a living body may be used to figure out a position of the distal end of the insertion portion relative to the living body and determine a collection region from which a specimen is to be collected, or a collection region may be determined using image analysis by identifying a direction of observation via the image pickup section.

The control section 11 can control respective sections of the specimen acquisition apparatus 10. The control section 11 may include a field programmable gate array (FPGA) or may be one that includes a non-illustrated processor such as a CPU and operates according to programs held in a non-illustrated memory, in conjunction with, e.g., a particular circuit.

The drive section 16 may include, for example, a drive mechanism configured to bend a bending portion of the insertion portion of the endoscope. An operation portion 13 accepts a user operation and supplies an operation signal based on the user operation to the control section 11. Consequently, the control section 11 may be able to change an image pickup direction inside a subject by controlling the drive section 16 according to a user operation. For example, the insertion portion of the endoscope in which the image pickup device is disposed may be able to be bent via a user operation, in a bending direction according to the user operation. Change of the image pickup direction is not limited to bending, and the bending portion may be expressed as a direction changing portion.

In the image input section 12, a direction determination section 12a is provided. The direction determination section 12a can determine an image pickup direction and/or a line of sight in image pickup and output a result of the determination to the control section 11. For example, the direction determination section 12a may determine a changed image pickup direction of the direction changing portion and/or a bending angle of the bending portion via the control section from outputs of a switch, a sensor and/or an encoder, or may determine an image pickup direction using, e.g., a magnetic coil employed in a known endoscope insertion shape observation apparatus.

In the control section 11, a file creation section 11a is provided. The file creation section 11a can create a file of image data acquired by the image input section 12 and various pieces of information pertaining to the shooting, according to predetermined rules. Here, an image file created by the file creation section 11a is referred to as "OM file". The file creation section 11a can provide a created image file to a recording section 14 to record the image file in the recording section 14.

In this file creation, the file creation section 11a can provide related information indicating what the image is like to the image file to record the related information in the image file. If various pieces of auxiliary information are provided to an image and the image is made to be able to be referred to in common, information linkage can be provided across devices. The file creation section 11a can record information indicating a relation between an image and cells as related information. For example, the related information includes, e.g., information indicating which region of which patient the image indicates and/or which treatment instrument of which endoscope was used for the acquisition. A part from which an object to be examined was collected and a feature of the object to be examined, etc., can be determined according to the apparatus and the treatment instrument, and in detailed examination, an examination can be conducted using results of the determination. Also, in an examination of cells (specimen) acquired by a biopsy, times such as a time of the cell acquisition and a time of start of the examination are also important, and thus, information on times of collection and biopsy of a tissue or the like is also included as the related information. Also, information on a clinician who collected the tissue or the like for the biopsy and information on a hospital name can be considered as the related information. In brief, as the related information, various types of information that can be considered as effective in respective medical institutions, etc., that deal with a collected tissue such as cells and other subjects themselves and images at the time of acquisition of the collected tissue such as cells and the other subjects can be included.

Of the related information, information on a specimen, that is, various types of information relating to treatments for the specimen such as collection, examination, observation and cultivation of the specimen is referred to as specimen information. Provision of specimen information to an image file enables obtaining information effective for various treatments for the specimen.

Here, the related information is information that is also effective for cases other than cases where processing for a collected tissue such as cells or other subject is performed, and related information may be added to all of images for which an image file is created to create the image files. Also, the file creation section 11a may add related information only to images at the time of acquisition of a subject such a cell from among image files to be created.

If an image file is one based on an image at the time of acquisition of a collected tissue such as cells or other subject, the file creation section 11a adds information indicating that the image file includes an image at the time of acquisition of a tissue such as cells or another subject, for example, a biopsy flag, to the image file. This biopsy flag also falls under the above-described specimen information. For example, the file creation section 11a may cause a biopsy flag or a treatment flag to be included in related information as specimen information. The biopsy flag or the treatment flag may be created by analyzing a change in an image to determine a particular shape change or movement of a particular instrument or a treatment instrument, or determining a particular operation of a device or determining, e.g., bleeding and providing a result of the determination as information. Furthermore, the biopsy flag or the treatment flag may be created by voice recognition and analysis of, e.g., a doctor's voice obtained via a microphone. Also, e.g., a patient's voice also serves as a reference for diagnosis and examination. Recording such information can contribute to identification of the collected object, or post-surgery remedy and further examination. Since detail specialization of medical devices according to diseased parts have been advancing, provision of information on a device or an apparatus and accessories of the device or the apparatus enables, e.g., identification of a diseased part.

Furthermore, it is possible that, e.g., a surgeon operates the operation portion 13 to provide an instruction for a timing for image acquisition by the image input section 12. In this case, the file creation section 11a can create an image file of an image acquired by the image input section 12 according to the instruction from the surgeon, as an image at the time of cell acquisition.

Furthermore, in the present embodiment, in movie shooting using an endoscope, an image at the time of specimen acquisition is automatically detected from sequentially-shot images to create an image file at the time of specimen acquisition. For this detection, a specimen state determination section 11b, which serves as a treatment detection section, is provided. The specimen state determination section 11b may also determine whether or not it is the time of specimen acquisition, according to operation of the treatment portion 16a. Also, the specimen state determination section 11b may determine whether or not it is the time of specimen acquisition, according to image analysis of an image that is being picked up from the image input section 12. For example, the specimen state determination section 11b may detect an image part of, e.g., a polyp by image recognition and determines that it is the time of specimen acquisition when a change in which an image feature of, e.g., the polyp disappears from the image part occurs.

In other words, in order to determine a treatment on a living body when an object to be observed such as a polyp is collected as described above, it is possible that an image feature section is provided and the image feature section determines a particular image feature and temporal change of the image feature from images obtained from the image pickup step to determine the treatment. Also, for determining an image feature of a treatment instrument or an image feature of a living body tissue from images obtained in the image pickup step according to such image feature, it is preferable to enable reference to image feature database for such determination. The image feature database is not required to be provided in the apparatus but may be recorded in a recording section in the apparatus. The same applies to voices, and for voices as well as images, a feature determination section may use voices or images stored in the apparatus or may also use voices or images provided outside the apparatus through linkage. An image file provided with information at the time of specimen collection enables easy extraction of an image necessary for an examination of a specimen taken from a living body and to be examined in, e.g., a different institution at a site distant from the living body, increasing accuracy in specimen examination. Because of digitalization of apparatuses, a countless number of shot images of a living body are provided, and thus, such contrivance for collection of an object to be examined is important.

Upon obtaining a result of the determination of whether or not the image is one at the time of specimen acquisition from the specimen state determination section 11b, the file creation section 11a may create an image file of a picked-up image from the image input section 12 as an image at the time of cell acquisition. For example, the file creation section 11a may create an image file of an endoscopic movie in a predetermined time period including a point of time of specimen acquisition as an image at the time of cell acquisition or create an image file of at least either of still images immediately before and immediately after specimen acquisition as an image at the time of cell acquisition.

Consequently, when a movie is shot via the endoscope, the file creation section 11a can create an image file of an image at the time of cell acquisition together with related information, while recording the movie in the recording section 14 as a movie file.

As described above, based on the idea that shooting an image of a living body at the time of collection of a subject (which may be a time before, after or during the collection) and recording a history of the subject after separation from the living body as image data (the data is sometimes effective not as the data itself but as auxiliary information-provided file) are important for determination in examination and/or subsequent treatment, the present invention can be expressed as an image file creation method including: an image pickup step of picking up an image of a living body; a treatment detection step of detecting a treatment related to the living body; and an image file creation step of creating an image file for image data obtained in the image pickup step, specimen information including information indicating that the image is an image relating to specimen collection by the treatment related to the living body being provided to the image file according to a result of the detection in the treatment detection step. A further description will be provided below with a technique of collecting a specimen in an endoscopic examination and sending the specimen to a cell examination step described particularly in detail.

The recording section 14 can include a predetermined recording medium, and can record an image file from the file creation section 11a. Also, the recording section 14 includes a device ID recording section 14a and a patient ID recording section 14b. The device ID recording section 14a holds identification information (device IDs) for identifying the specimen acquisition apparatus 10 and/or the treatment portion 16a, and the patient ID recording section 14b holds identification information (patient IDs) for identifying a patient that is a subject. The control section 11 can read a device ID and a patient ID from the recording section 14, and the file creation section 11a can cause device ID and patient ID information to be included as related information.

In the specimen acquisition apparatus 10, a display section 18 is provided. The display section 18 may include, for example, an LCD, and displays an image provided from the control section 11 on a non-illustrated display screen. For example, the display section 18 can display an image that is being acquired by the image input section 12 or a reproduced image based on an image file read from the recording section 14 by the control section 11.

In the display section 18, an auxiliary display section 18a is provided. The auxiliary display section 18a can display an image obtained by superimposing an auxiliary display on an image provided from the control section 11, on the display screen of the display section 18. For example, the auxiliary display section 18a can provide information display based on information such as a device ID and/or a patient ID and/or other related information as the auxiliary display.

In the specimen acquisition apparatus 10, a clock section 19 is provided. The clock section 19 can generate time information and output the time information to the control section 11. Consequently, the file creation section 11a can create time information of the time of specimen acquisition as related information.

In the specimen acquisition apparatus 10, a communication section 15 is provided. The communication section 15 is controlled by the control section 11 and can access an image management apparatus 20 (see FIG. 2) on a non-illustrated network. The communication section 15 receives transmission data from the control section 11 and transmits the transmission data to the image management apparatus 20 on the network, and supplies reception data from the image management apparatus 20 on the network to the control section 11.

Figure 2:
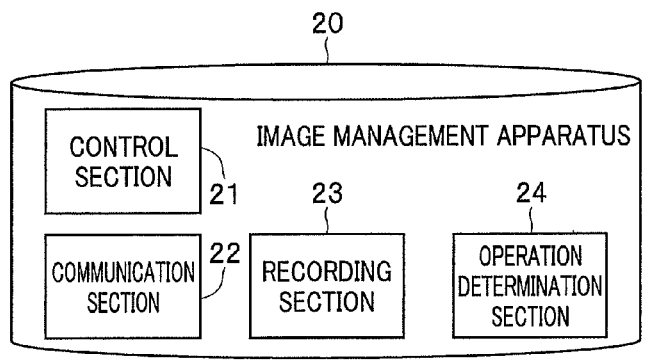
FIG. 2 is a block diagram illustrating a medical system in which an image file creation method according to an embodiment of the present invention is implemented.
Figure 3:
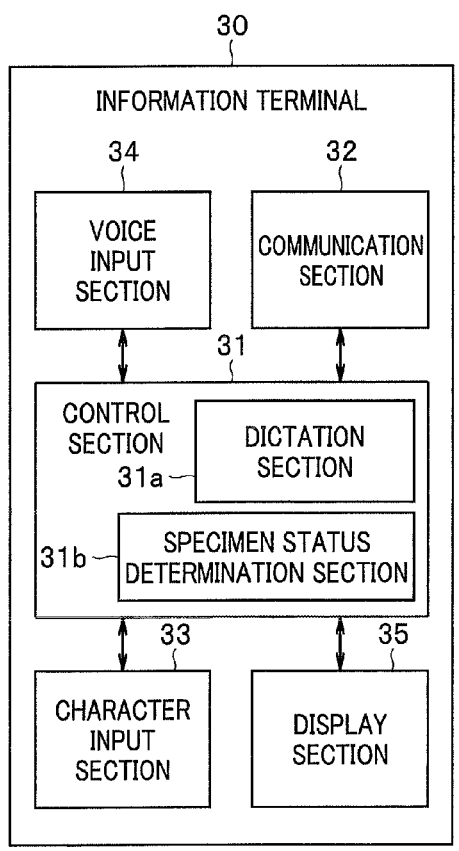
FIG. 3 is a block diagram illustrating a medical system in which an image file creation method according to an embodiment of the present invention is implemented.

FIGS. 2 and 3 are block diagrams each illustrating an image management apparatus 20 or an information terminal 30 included in a management system as a bio-related apparatus. The management system includes the image management apparatus 20 and the information terminal 30.

The image management apparatus 20 is a file server configured to hold database of image files, and as illustrated in FIG. 2, includes a control section 21, a communication section 22, a recording section 23 and an operation determination section 24.

The control section 21 controls respective sections of the image management apparatus 20. The control section 21 may include a non-illustrated processor such as a CPU and operate according to programs stored in a non-illustrated memory. The communication section 22 is controlled by the control section 21 and is connected to bio-related apparatuses in respective medical institutions, etc., the bio-related apparatuses connected to the network, and can receive data from the bio-related apparatuses and transmit data from the control section 21 to the respective bio-related apparatuses.

The recording section 23 includes a predetermined recording medium, and is controlled by the control section 21 to record image files from the respective medical institutions, etc. The control section 21 can read the image files recorded in the recording section 23 and transmit the image files to the bio-related apparatuses in the respective medical institutions, etc., via the communication section 22.

The operation determination section 24 receives an input of operation information from an information terminal 30 via the communication section 22, and instructs the control section 21 to perform control designated by the operation information. Consequently, the control section 21 can perform not only reading, modification, update, writing, etc., of an image file, but also creation and recording of a new image file, according to information from the information terminal 30. For example, the image management apparatus 20 can read an image file stored in the recording section 23 and adds a biopsy flag (e.g., a signal enabling identification of the relevant image file as an image file relating to a treatment or work of extracting a part of, e.g., a diseased part via, e.g., an instrument in order to further examine the part by a different method using, e.g., a microscope) to the read image file or create a new image file with new information added or information modified based on the read image file.

Also, related information that can be provided in the specimen acquisition apparatus 10 is limited. Therefore, the image management apparatus 20 can set new or additional related information in an image at the time of specimen acquisition with no related information provided or an image at the time of specimen acquisition with related information already provided.

Access to the recording section 23 of the image management apparatus 20 can be made by the information terminal 30 illustrated in FIG. 3. The information terminal 30 is intended to perform reading, modification, update, writing, new creation, etc., of data recorded or to be recorded in the image management apparatus 20, and for example, includes any of various types of information terminals such as a personal computer and a tablet terminal. Note that the information terminal 30 configures the management system jointly with the image management apparatus 20, but may be connectable to the image management apparatus 20 via the network, and can be disposed in each of one or more medical institutions, etc.

A control section 31 of the information terminal 30 controls respective sections of the information terminal 30. The control section 31 may be one that includes a non-illustrated processor such as CPU and operates according to programs stored in a non-illustrated memory.

In the information terminal 30, a communication section 32 is provided. The communication section 32 is controlled by the control section 31 to enable transmission/reception of information to/from the communication section 22 of the image management apparatus 20. A character input section 33 is controlled by the control section 31 and inputs character information based on a user operation. A voice input section 34 is controlled by the control section 31 and inputs voice information based on a user operation. The control section 31 includes a dictation section 31a, and the dictation section 31a recognizes inputted voice information to produce text information.

A display section 35 is controlled by the control section 31 and displays an image from the control section 31 on a non-illustrated display screen. For example, the control section 31 can display an image based on an image file read from the image management apparatus 20 on the display screen of the display section 35. In this case, the control section 31 can also provide information display based on related information corresponding to the read image file on the display screen.

For example, the control section 31 can also display an image at the time of specimen acquisition on the display screen. Furthermore, the control section 31 can produce related information obtained by modification of, and/or addition to, related information included in a read image file based on information from the character input section 33 or information from the voice input section 34 to create a new image file (hereinafter also referred to as "OI file") from the read image file. In other words, an OI file is a file created from an image file (for example, an OM file) recorded in the recording section 23 of the image management apparatus 20.

Note that, although it has been described that the control section 31 creates a new OI file from an OM file, the control section 31 may perform modification of, or addition to, an OM file based on information from the character input section 33 or information from the voice input section 34 to obtain the OM file with related information updated.

In the specimen acquisition apparatus 10 in FIG. 1, the specimen state determination section 11b is provided, and an image file of an image at the time of specimen acquisition together with related information is created. However, the specimen state determination section 11b may fail in detection of specimen acquisition, and also, an image picked up by an endoscope including no specimen state determination section 11b may be stored in the recording section 23. Such image file may be provided with no biopsy flag even if the image file includes an image at the time of cell acquisition.

In such case, a biopsy flag can be provided to an OI file created by the information terminal 30. For example, the control section 31 can display an image that is unknown regarding whether or not the image is an image at the time of specimen acquisition, on the display screen of the display section 35. Even for an image with no biopsy flag provided, an operator can determine whether or not the image is an image at the time of specimen acquisition by viewing the image on the display screen. In this case, the operator can input information indicating that an image that is being displayed is an image at the time of specimen acquisition via the character input section 33 or the voice input section 34. Upon the input of such information, the control section 31 adds information identifying the image that is being displayed as an image at the time of specimen acquisition (for example, a biopsy flag) to the image file.

An image file enables organizing various other data in a particular format and recording the data, and thus, not only an image itself but also patient ID information, hospital ID information, attending doctor ID information, ID information of an apparatus and/or a treatment instrument, collection time and date information, collected region (organ) information determined from the apparatus and/or the treatment instrument, and accompanying information such as a collection position are packaged in a single image file, which is convenient for comprehensive utilization of these pieces of information. Images provide a large amount of information that can be recognized by humans, and thus are highly searchable and can also be used for determination of, e.g., the time and the extent of an examination to be conducted, by specifying a patient and/or a hospital. Also, centralized data management of relationships between examination objects and examination results after detailed examinations allows doctors and experts to easily make judgment.

Note that the control section 31 can also create an image file (OI file) obtained by deleting a biopsy flag from an image file (OM file) with the biopsy flag provided, based on a user operation. Also, even if a biopsy flag is provided in an OM file, the control section 31 may newly provide an additional biopsy flag when an OI file is created. For example, if an OM file and an OI file are different from each other in provided biopsy flag, an operation in which the biopsy flag in the OI file is determined as effective is also possible.

Also, the control section 31 includes a specimen state determination section 31b. The specimen state determination section 31b may determine an image at the time of specimen acquisition from a movie that is being displayed on the display screen of the display section by means of operation that is similar to the operation of the specimen state determination section 11b. Consequently, even if an image file recorded in the recording section 23 of the image management apparatus 20 is provided with no biopsy flag despite the image file including an image at the time of cell acquisition, an image file (OI file) with a biopsy flag automatically provided by means of image recognition can be created. Also, if information indicating that the image is an image at the time of cell acquisition is inputted via the character input section 33 or the voice input section 34, the specimen state determination section 31b can analyze the information from the character input section 33 or the voice input section 34 to determine that the image is an image at the time of cell acquisition and create an image file (OI file) with a biopsy flag automatically provided. For example, an operator may determine that an image that is being displayed is an image at the time of cell acquisition, by saying words such as "biopsy" or "specimen acquisition".

Upon obtaining a result of the determination of the time of specimen acquisition from the specimen state determination section 31b, the control section 31 may create an image file of the picked-up image that is being displayed, as an image at the time of specimen acquisition. For example, the control section 31 may create a new image file of an endoscopic movie in a predetermined time period including a point of time of specimen acquisition in the image that is being picked up, as an image at the time of specimen acquisition or may create a new image file of at least either of still images immediately before and immediately after the time of specimen acquisition, as an image at the time of specimen acquisition.

In the present embodiment, in sending of a specimen obtained by the specimen acquisition apparatus 10 to an examination institution, information associating the specimen to be sent and an image at the time of cell acquisition with each other can be added to an image file based on the image at the time of cell acquisition using the information terminal 30. For example, it is possible that identification information (specimen ID) for identifying the specimen to be sent is set and the specimen ID is added to the image file. For example, the control section 31 creates an image file (OI file) with the specimen ID information added in related information.

Here, if the control section 21 of the image management apparatus 20 updates an OM file according to an instruction from the information terminal 30, the control section 21 of the image management apparatus 20 may transmit the updated OM file to a bio-related apparatus in each medical institution, etc., to update data in the bio-related apparatus.

Figure 4:
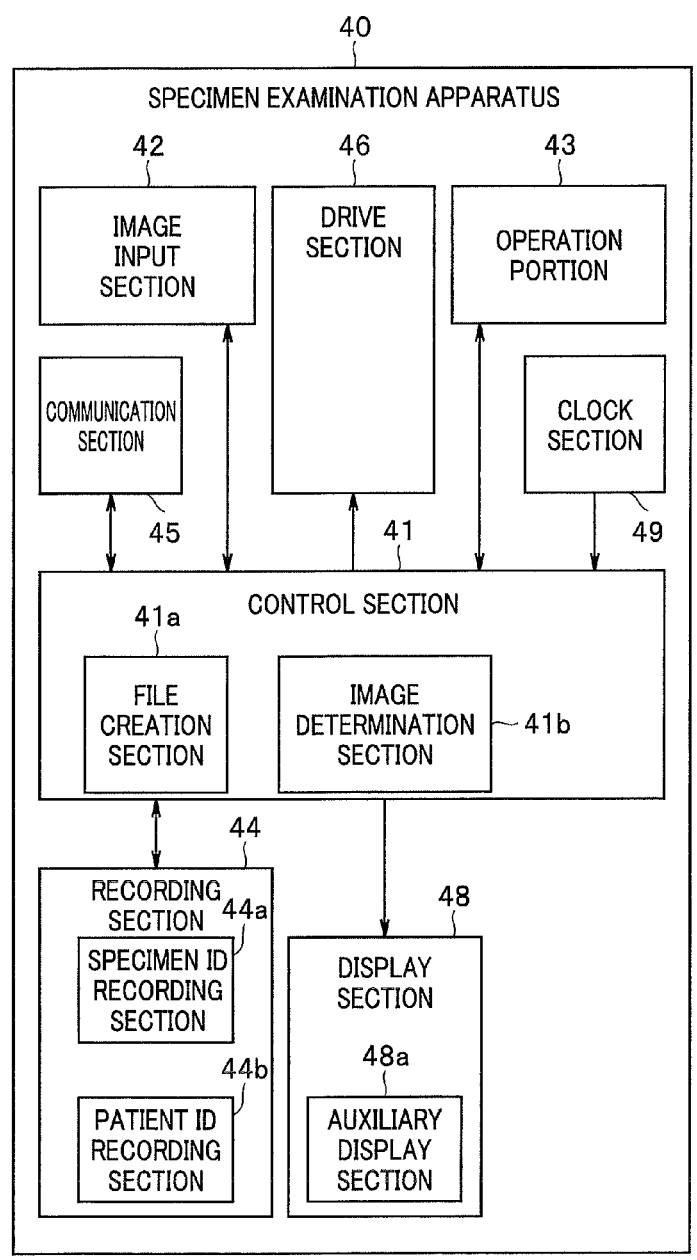
FIG. 4 is a block diagram illustrating a medical system in which an image file creation method according to an embodiment of the present invention is implemented.

FIG. 4 is a block diagram illustrating a specimen examination apparatus 40, which is a bio-related apparatus. The specimen examination apparatus in FIG. 4 is an apparatus to be operated, for example, by a laboratory technician to examine a specimen in an examination institution. For the specimen examination apparatus 40 in FIG. 4, an electronic microscope may be employed.

The control section 41 can control respective sections of the specimen examination apparatus 40. The control section 41 may be one that includes a non-illustrated processor such as a CPU and operates according to programs held in a non-illustrated memory.

The specimen examination apparatus 40, which serves as a cell examination apparatus, includes an image input section 42. The image input section 42 can pick up an image of a specimen mounted on a non-illustrated table to acquire the picked-up image. The image input section 42 may be one that acquires a pick-up image of a subject via, for example, a non-illustrated image pickup device such as a CMOS sensor or a CCD sensor. The image input section 42 outputs the picked-up image of the specimen to the control section 41.

A drive section 46 can drive the table with the specimen mounted, horizontally or vertically. The drive section 46 outputs information on an amount of driving of the table to the control section 41. Consequently, the control section 41 can perceive which area of the specimen mounted on the table is being subjected to the image pickup.

In the control section 41, a file creation section 41a is provided. The file creation section 41a can create a file of an image acquired by the image input section 42. The file creation section 41a can provide the created image file to a recording section 44 to record the image file in the recording section 44.

The recording section 44 can include a predetermined recording medium and record an image file from the file creation section 41a. Also, the recording section 44 includes a specimen ID recording section 44a and a patient ID recording section 44b, and the specimen ID recording section 14a holds a specimen ID of an object to be examined, and the patient ID recording section 14b holds a patient ID of a patient from which a specimen to be examined was acquired.

An operation portion 43 accepts a user operation and supplies an operation signal based on the user operation to the control section 41. Consequently, the control section 41 may be able to control the drive section 46 according to the user operation to move the table. Also, the operation portion 43 may allow an input of a specimen ID and a patient ID, etc. The information on the specimen ID and the patient ID, etc., is provided to and recorded in the specimen ID recording section 44a or the patient ID recording section 44b of the recording section 44 by the control section 41. Here, inputting various types of information relating to the specimen to be examined, via the operation portion 43, may allow the control section 41 to record various types of information inputted in the recording section 23.

Note that the operation portion 43 may have a bar code reading function. For example, if a bar code indicating a specimen ID is added to, e.g., a package that stores a specimen, the specimen ID can be acquired by reading the bar code by means of the operation portion 43. The specimen ID read by the operation portion 43 is recorded in the specimen ID recording section 44a.

In the specimen examination apparatus 40, a communication section 45 is provided. The communication section 45 is controlled by the control section 41 and can access the image management apparatus 20 on the network. The communication section 45 receives transmission data from the control section 41, and transmits the transmission data to the image management apparatus 20 and supplies reception data from the image management apparatus 20 to the control section 41. Consequently, the control section 41 can receive an image file recorded in the recording section 23 of the image management apparatus 20. The control section 41 can provide the received image file to the recording section 44 to record the image file in the recording section 44.

The control section 41 can designate an image file to be read from the image management apparatus 20, based on, e.g., information on a specimen ID recorded in the specimen ID recording section 44a and/or a patient ID recorded in the patient ID recording section 44b. Consequently, an image file including an image relating to a specimen to be examined, for example, an image at the time of acquisition of the specimen to be examined can be retrieved via the network.

The file creation section 41a can create a new image file including an image based on an image file (OI file) downloaded from the image management apparatus 20 and a picked-up image from the image input section 42. Furthermore, the file creation section 41a can generate new related information including related information in the downloaded image file based on a user operation of the operation portion 43 and add the new related information to the created image file. The file creation section 41a can also provide the created new image file (hereinafter referred to as "OS file") to the recording section 44 to record the new image file in the recording section 44.

Furthermore, the control section 41 can transmit the OS file created by the file creation section 41a to the image management apparatus 20 on the network via the communication section 45. Consequently, the OS file is recorded in the recording section 23 of the image management apparatus 20. Here, the file creation section 41a may modify the OI file downloaded from the image management apparatus 20 with the picked-up image from the image input section 42 and the related information based on the user operation of the operation portion 43 without creating a new image file (OS file).

In the specimen examination apparatus 40, a clock section 49 is provided. The clock section 49 can generate time information and output the time information to the control section 41. Consequently, the file creation section 41a can produce time information at the time of a specimen examination as related information. The related information newly added by the file creation section 41a may include, e.g., information on an examination date and/or an examination result.

In the specimen examination apparatus 40, a display section 48 is provided. The display section 48 may include, for example, an LCD, and displays an image provided from the control section 41 on a non-illustrated display screen. For example, the display section 48 can display an image based on a downloaded OI file and an image acquired by the image input section 42.

In the display section 48, an auxiliary display section 48a is provided. The auxiliary display section 48a can display an image obtained by superimposing an auxiliary display on an image provided from the control section 41, on the display screen of the display section 48. For example, the auxiliary display section 48a can provide information display based on information such as a device ID and/or a patient ID and/or other related information as the auxiliary display.

Also, the information terminal 30 can provide an instruction to the control section 21 of the image management apparatus 20 to read an OS file recorded in the recording section 23, and create an OI file obtained by addition of predetermined modification to the OS file. This OI file is also recorded in the recording section 23 of the image management apparatus 20. As described above, each image file recorded in the recording section 23 can be edited using the information terminal 30. Also, if the control section 21 updates an OS file according to an instruction from the information terminal 30, the control section 21 may transmit the updated OS file to the bio-related apparatus in each medical institution, etc., to update data in the bio-related apparatus.

Figure 5A:
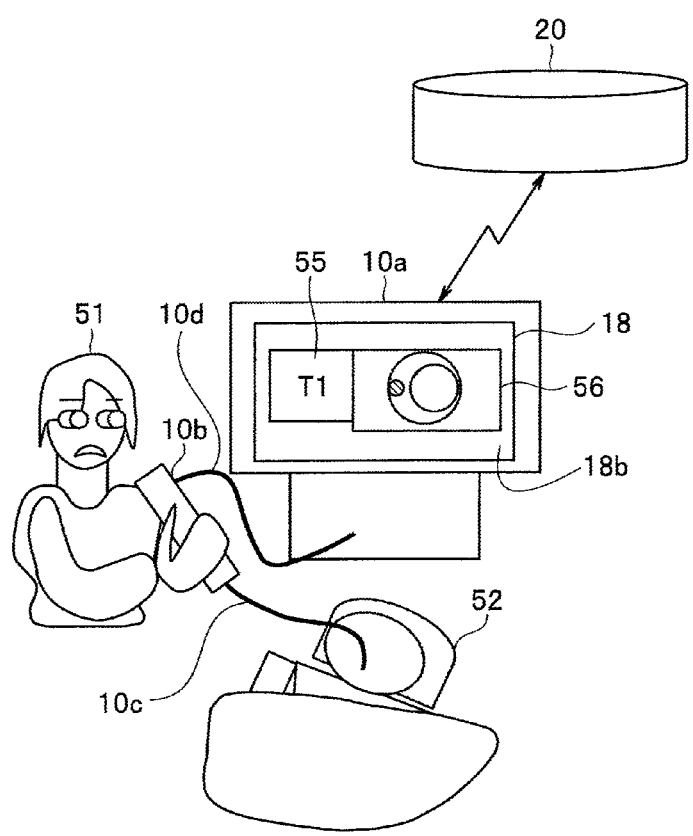
FIG. 5A is a diagram illustrating a manner of use of a bio-related apparatus.
Figure 5B:
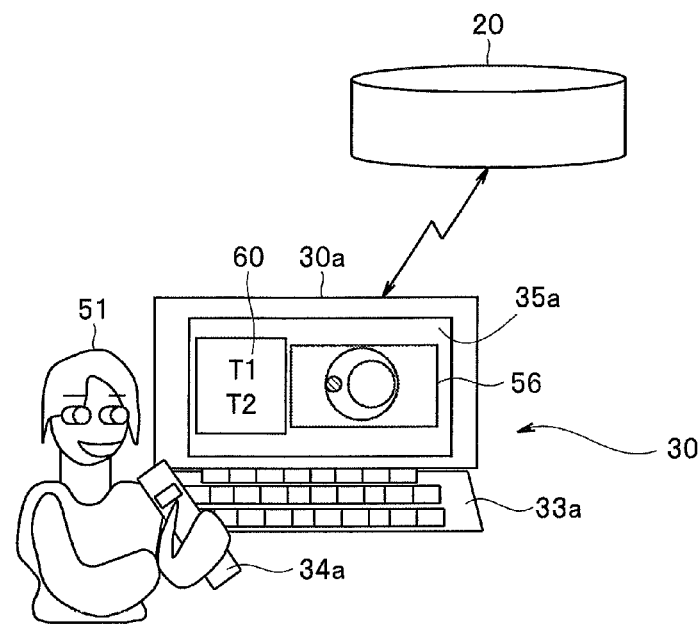
FIG. 5B is a diagram illustrating a manner of use of a bio-related apparatus.
Figure 5C:
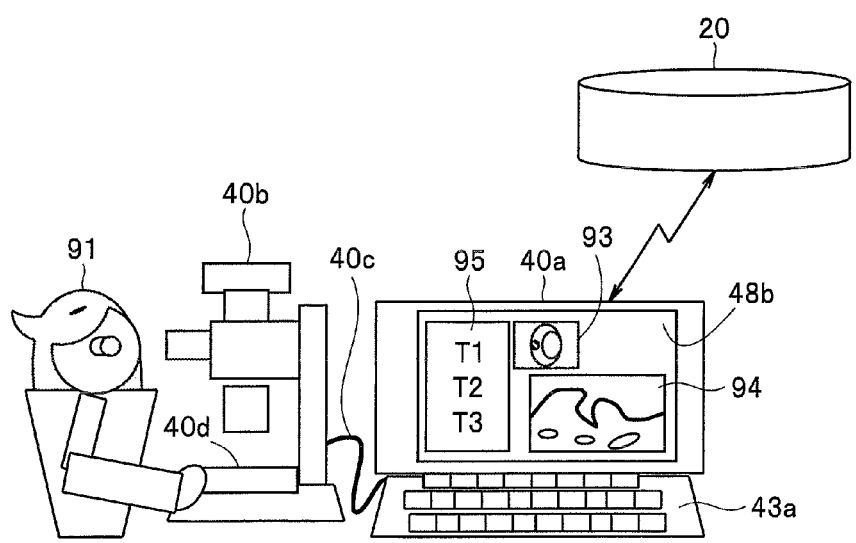
FIG. 5C is a diagram illustrating a manner of use of a bio-related apparatus.

Next, operation of the embodiment configured as described above will be described with reference to FIGS. 5A to 5C, FIGS. 6A to 6D and FIGS. 7 to 9. FIGS. 5A to 5C are diagrams illustrating manners of use of respective bio-related apparatuses in FIGS. 1, 3 and 4, FIGS. 6A to 6D are diagrams each illustrating an example of screen display, and FIGS. 7 to 10 are flowcharts for describing operation of an embodiment.

Figure 7:
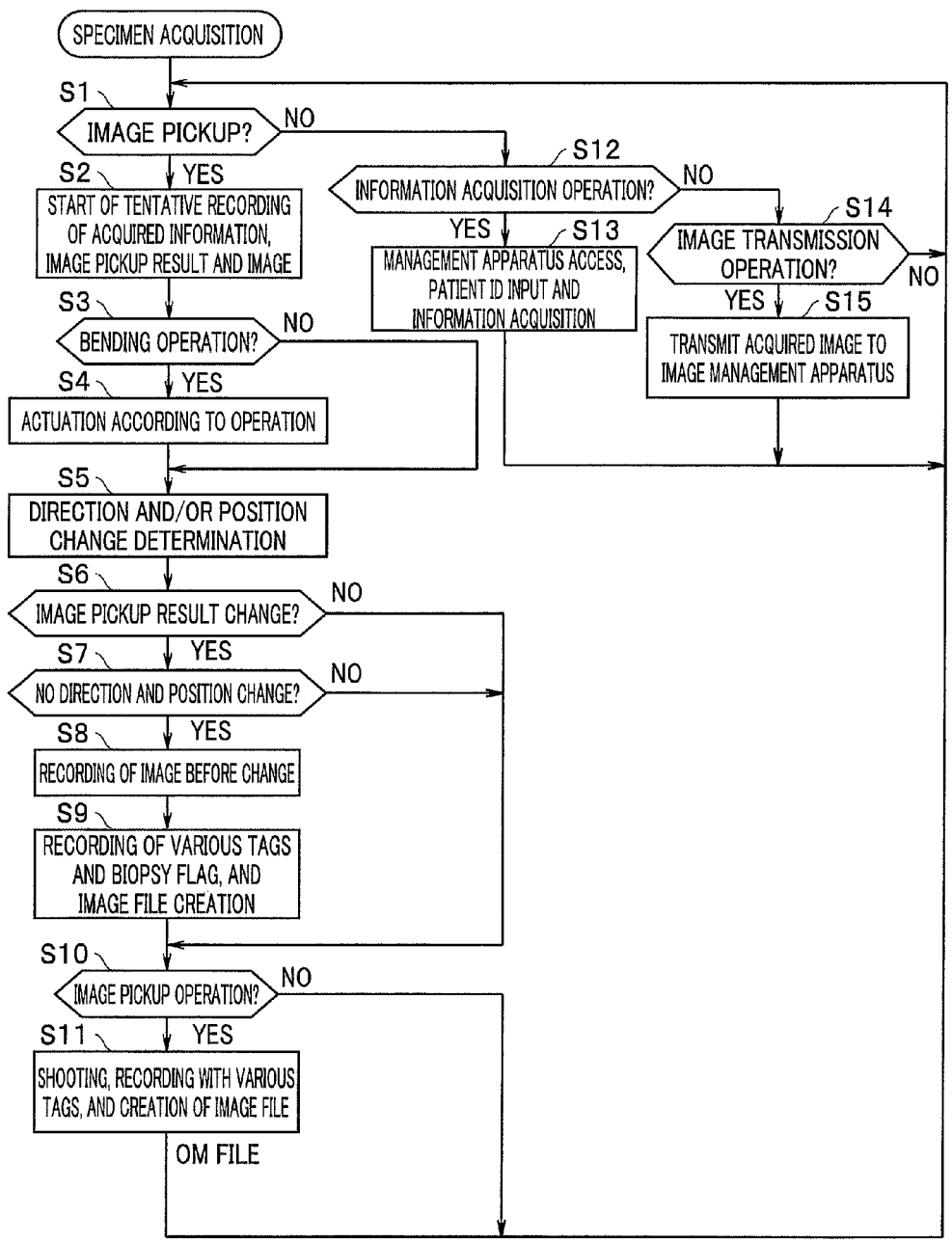
FIG. 7 is a flowchart for describing operation in an embodiment.

In step S1 in FIG. 7, the control section 11 in the specimen acquisition apparatus 10 determines whether or not an instruction to pick up an image is provided by a surgeon. If no instruction to pick up an image is provided, the control section 11 performs an information acquisition operation in step S12. For example, the control section 11 may acquire information by means of an input operation via the operation portion 13 or may access a non-illustrated management terminal and acquire various types of information. Examples of the acquired information include information such as a patient ID and a device ID. The control section 11 provides the acquired information to the recording section 14 to record the acquired information in the recording section 14.

An example in which an endoscope including an operation portion 10b and an insertion portion 10c illustrated in FIG. 5A is employed as the specimen acquisition apparatus 10 will be described. As illustrated in FIG. 5A, a clinician 51 inserts the insertion portion 10c of the endoscope into the body of a patient 52 lying on a bed from the mouth. The clinician 51 grasps the operation portion 10b of the endoscope and shoots an image of the inside of a subject in the patient 52. An image picked up by the endoscope is supplied to the control section 11 housed in a chassis 10a of the specimen acquisition apparatus 10 via a cable 10d. Upon the clinician 51 performing an operation to pick up an image, the control section 11 makes the transition of the processing from step S1 to step S2 to provide the picked-up image to the recording section 14 and start tentative recording of the acquired information and image. Also, the control section 11 displays the picked-up image and various types of information acquired on a display screen 18b of the display section 18. For various types of information, information relating to a patient ID and/or an examination may be employed. Also, related information may be included in the information to be displayed.

In step S3, the control section 11 determines whether or not a bending operation is performed. If a bending operation is performed, the control section 11 controls the drive section 16 to actuate the insertion portion 10c according to an operation (step S4). Upon change in direction and/or position of an image pickup device provided in the insertion portion 10c as a result of, e.g., an operation to insert and/or bend the insertion portion 10c, the control section 11 determines the change (step S5).

It is considered that no biopsy is performed during insertion of the insertion portion 10c into the subject and a biopsy is performed after movement of the insertion portion 10c stopped and no change of an image pickup range came to be seen any longer. The specimen state determination section 11b determines whether or not an image pickup result has a change in step S6 and determines whether or not the image pickup device has a change in direction and position in step S7. If the specimen state determination section 11b determines that the image pickup device does not change in direction and position and an image part of, e.g., a polyp in the picked-up image have a change, the specimen state determination section 11b makes the transition to step S8 to record the image before the change in the image part of, e.g., the polyp in the picked-up image in the recording section 14 as an image at the time of cell acquisition.

For example, the treatment portion 16a includes biopsy forceps inserted inside the insertion portion 10c, and the clinician 51 operates the biopsy forceps to extract the specimen such as the polyp from the inside of the subject. Then, the specimen state determination section 11b detects that the image part of the polyp has a change in step S6, and if the image pickup device has no change in direction and position, the specimen state determination section 11b records the picked-up image before removal of the specimen such as the polyp in the recording section 14 as an image at the time of cell acquisition in step S8.

As described above, provision of an image file creation method including: an image pickup step of picking up an image of a living body (origin of a collected object); a treatment detection step of detecting a treatment related to the living body (origin of the collected object); and an image file creation step of creating an image file for image data obtained in the image pickup step, specimen (collected object) information including information indicating that the image is an image relating to specimen collection by the treatment related to the living body (origin of the collected object) being provided to the image file according to a result of the detection in the treatment detection step enables enhancement in reliability and/or searchability of, e.g., results of various examinations using the collected object. Also, the type of the collection can be determined from the apparatus and the treatment instrument used in the collection, and thus, e.g., an examination of a tissue subjected to processing according to the type of the collection tissue can be performed. Such information enables designation or identification of, e.g., an apparatus, a device and/or a technique to be used in a biopsy and thus enables enhancement in reliability.

FIG. 5A illustrates a state in which an image at the time of cell acquisition is displayed on the display screen 18b of the display section 18. As illustrated in FIG. 5A, the control section 11 displays a picked-up image 56 on the display screen 18b of the display section 18. Also, the auxiliary display section 18a displays various types of information 55 that can be designated as a tag T1 on a part of the display screen 81b. Here, as the tag T1, various types of information relating to a patient ID and/or an examination may be employed. Also, as the tag T1, related information may be included in the display.

In step S9, the file creation section 11a creates an image file of the image at the time of cell acquisition with the related information added. The related information in this case includes a biopsy flag. Note that, although in the example in FIG. 7, an example in which a picked-up image immediately before specimen acquisition is acquired as an image at the time of cell acquisition is indicated, an image immediately after specimen acquisition may be acquired as the image at the time of cell acquisition, and a plurality of picked-up images immediately before and after specimen acquisition may be acquired at images at the time of cell acquisition.

A result of picking up an image of an origin (living body) of the collected object is preferably an image from which, e.g., what a diseased part or a lesion looked like or what the health condition was like can be seen when the image is viewed later. For a color and/or a shape of the collected object and/or a periphery of the collected object, the color and/or the shape that enables a feature to be easily perceived may be selected. For that purpose, a shape and/or a color, etc., typical to the relevant region may be recorded in the database and comparison with the shape and/or the color is performed to select a color and/or a shape with reference to similarity to the shape and/or the color. An image having largest change in color of the periphery of the collected object in the image or an image including many points of change in, e.g., a contour and thus having a large amount of information in shape may be selected. Or, since an object to be examined in, e.g., a biopsy loses its original shape as a result of, e.g., staining and/or slicing for unit observation, an image having largest change in color of the collected object itself in the image or an image including many points of change in, e.g., a contour and thus having a large amount of information in shape may be selected. Also, the shape of the collected object itself may be a shape unique to a particular case, and in an examination for such suspected case, an image before collection of a subject often serves as a useful reference also in a subsequent examination. An examination method can be changed depending on, e.g., whether or not bleeding occurs. Several methods for biopsy (tissue collection) are provided, and in some cases, cytological diagnosis for cells and tissue diagnosis involving tissue extraction are distinguished from each other and tissue diagnosis is regarded as biopsy; however, here, the description is provided with cytological diagnosis and tissue diagnosis collectively referred to as "biopsy". Also, cells can be collected from, e.g., secretion, and the description will be continued with such cell collection included in "biopsy". In cytological diagnosis, a method called fine-needle aspiration is provided, needle biopsy in which a tissue is collected using a thicker needle is also provided, and surgical biopsy for surgical collection is also provided. Surgical biopsy enables observation of a histology of an entire lesion and has an accuracy that is higher than an accuracy of needle biopsy in which an entire lesion is estimated to perform diagnosis. Also, in fine-needle aspiration cytology, it is necessary to estimate an entire lesion from a cell image, and thus it is important that the diagnosis method differs depending on whether or not an entire lesion can be viewed. In some cases, a re-examination becomes necessary as a result of refine-needle aspiration cytological diagnosis or needle biopsy, and provision of such history information enables increasing in accuracy of diagnosis in total. In other words, as the step of providing specimen information, it is preferable that the step of determining biopsy type information to determine which method from among these biopsy methods is selected be provided. The biopsy type information may be determined by determining a shape of a used device via an image or determining a process of an operation from an image, or may be determined by recognition of a doctor's voice using a later-described dictation technique.

In step S10, the control section 11 determines whether or not the clinician 51 performs an operation to pick up an image. If the clinician 51 performs an image pickup operation, in step S11, the file creation section 11a adds related information to an image from the image input section 12 and creates an image file of the image. The related information in this case may include no biopsy flag. Here, if the clinician 51 performs the image pickup operation together with an operation to designate the image as an image at the time of cell acquisition, a biopsy flag is included in the image file to be recorded.

As described above, this image file creation method includes the step of determining biopsy type information such as described above in providing the specimen information. An image in a biopsy flag-included image file created here is preferably in a format that enables association with a final detailed examination result. Consequently, a clinician can easily refer to a result of an examination in which the clinician did not necessarily present, from images viewed and record by the clinician, and can make a correct diagnosis and provide a proper instruction to a patient. In other words, the above image file creation method includes the step of creating an association area to be associated with a biopsy result or a tissue examination result.

Also, in step S12, if no operation to acquire information is performed, the control section 11 determines whether or not an image transmission operation is performed in step S14. If a user performs the transmission operation, the communication section 15 is controlled by the control section 11 to transmit the image file (OM file) recorded in the recording section 14 to the image management apparatus 20 and record the transmitted image file (OM file) in the image management apparatus 20 in step S15.

The control section 21 in the image management apparatus 20 provides the image file (OM file) from the specimen acquisition apparatus 10 to the recording section 23 and record the image file (OM file) in the recording section 23. The image file recorded in the recording section 23 includes the image picked up by the specimen acquisition apparatus 10 such as the endoscope and the related information related to the image. In the present embodiment, the image file recorded in the recording section 23 can be read by a plurality of information terminals 30 that can access the image management apparatus 20.

The specimen collected by the clinician 51 via the biopsy is not associated with the image at the time of cell acquisition by the specimen acquisition apparatus 10. In the present embodiment, for example, the clinician 51 associates the specimen collected via the biopsy and the image at the time of cell acquisition at the time of acquisition of the specimen, using the information terminal 30.

FIG. 5B illustrates an example in which the information terminal 30 includes the chassis 30a in which the control section 31, etc., are housed, a keyboard 33a included in the character input section 33 and a dictation microphone 34a included in the voice input section 34. When the clinician 51 activates the information terminal 30, in step S21 in FIG. 8, the control section 31 causes the display section 35 to provide a list display of applications (application list display). When the clinician 51 selects and activates a clinical application (hereinafter referred to as "clinical application"), the control section 31 makes the transition from step S22 to step S23 and displays an input screen of the clinical application. For example, for patient identification, a patient ID can be inputted on this input screen.

Here, in step S32, the control section 21 in the image management apparatus 20 determines whether or not access is made via a network, and if access is made, information is, e.g., recorded, added or transmitted according to the access. Also, if no access is made, the control section 21 executes another application (step S34).

Upon an input of a patient ID by the clinician 51, the control section 31 in the information terminal 30 makes the transition from step S24 to step S25 and provides related information acquisition display for selecting information relating to a patient designated by the patient ID, on the display screen 35*a*. It can be considered that a plurality of images are recorded for each of various examinations and each of surgical operations and the like for one patient. The clinician 51 can select one image file from among a plurality of image files acquired at the time of a biopsy by, for example, designating a date of the biopsy. For example, the control section 31 provides thumbnail display of minified images of images based on the plurality of image files acquired at the time of the biopsy (step S26). When the clinician 51 selects a predetermined thumbnail indication, the control section 31 makes the transition from step S27 to step S28 to provide enlarged display of an image based on the selected image file.

Figure 6A:
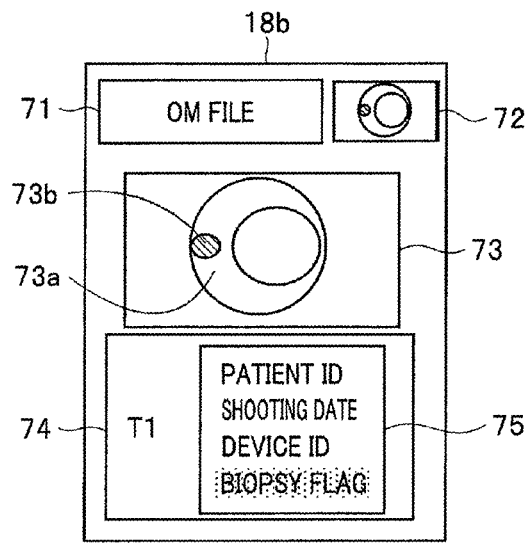
FIG. 6A is a diagram illustrating an example of screen display.

FIG. 6A illustrates an example of an image displayed on the display screen 35*a* of the display section 35 of the information terminal 30 based on an image file obtained at the time of acquisition of a specimen. As illustrated in FIG. 6A, in an upper portion of the display screen 35*a*, a display 71 of "OM file" indicating that the image that is being displayed is one based on an image file created by the specimen acquisition apparatus 10 and a thumbnail display 72 of the image are provided, in a center portion, an enlarged display 73 of the image is provided, and in a lower portion, a related information-based display 74 based on related information is provided.

In the related information-based display 74, "T1" indicates that the related information is one obtained by the specimen acquisition apparatus 10, which is designated by the tag T1. Also, in a character display area 75 of the related information-based display 74, as related information, character strings relating to a patient ID, a shooting time and date, a device ID and a biopsy flag are displayed.

From the display of the biopsy flag in the character display area 75, it can be understood that an image in the enlarged display 73 is an image at the time of cell acquisition. The image at the time of cell acquisition is an image obtained by the image input section 12 of the specimen acquisition apparatus 10, and a part of an image 73*a* of the inside of a subject includes an image part of a biopsy object part 73*b* such as a polyp.

Here, in step S27, if no thumbnail is selected, the control section 31 determines whether or not a finding input is provided in step S36. Upon generation of a finding input, finding information is associated with the patient ID (step S37). If the control section 31 determines in step S38 that no return operation is performed, in step S25, the control section 31 causes the related information including the finding information to be displayed.

Here, the clinician 51 associates the image at the time of cell acquisition indicated by the enlarged display 73 provided in step S28, with the specimen acquired by the biopsy. In the present embodiment, for example, a specimen acquired by a biopsy is housed in a non-illustrated predetermined package and sent to an examination institution, and the package is labeled with character strings or bar codes or the like indicating a specimen ID and a biopsy flag for identifying the specimen. In the present embodiment, an image at the time of cell acquisition and a specimen are associated with each other by addition of a specimen ID to an image file of the image at the time of cell acquisition. Here, for information for specimen identification and association with an image at the time of cell acquisition, various types of information, which is not limited to a specimen ID, such as a patient ID, a region subjected to a biopsy and/or a time and date of the biopsy can be employed. As the above step of providing specimen information, the step of determining biopsy type information is provided, and thus, the information helps in performing a detailed examination according to each tissue collection method.

An input operation for association is performed via, e.g., the keyboard 33*a* or the dictation microphone 34*a*. The control section 31 determines whether or not a finding input is provided in step S29, and if an input operation is performed by the clinician 51, in step S30, the control section 31 performs operation to add information based on the input operation to the image file as related information. As a result of the clinician 51 inputting the specimen ID, the specimen ID is added to the image file including the image that is being displayed, as related information.

Also, in step S31, the control section 31 determines whether or not a text or a voice "biopsy" is inputted by the character input section 33 or the voice input section 34. For example, when the clinician 51 says "biopsy" toward, e.g., the dictation microphone 34*a*, the dictation section 31*a* determines that the image that is being displayed is an image at the time of cell acquisition. In this case, the control section 31 adds a biopsy flag to the read image file as related information. Consequently, even if no biopsy flag is added to an image at the time of cell acquisition in the specimen acquisition apparatus 10, a biopsy flag can be added in the information terminal 30. Also, the control section 31 can delete a biopsy flag from an image file of an image at the time of cell acquisition, the image being added with the biopsy flag in the specimen acquisition apparatus 10. Furthermore, it is also possible to use a biopsy flag added to an image file in the specimen acquisition apparatus 10 only for image file search and use only a biopsy flag added in the information terminal 30 for determination of an image at the time of cell acquisition.

Since "biopsy" means specimen acquisition (tissue collection), it should be understood that a voice "specimen collection" or "tissue collection" is also possible, and a dictionary for voice determination is provided in advance in, e.g., the system or the recording section. Artificial intelligence may learn such voices while performing comparison among a person who performs collection, an expression particular to a person who orders the collection and determination of processing performed. It should be understood that this voice recognition can effectively be utilized for finding input. As the above step of providing specimen information, the step of determining biopsy type information is provided; however, this case is an example in which the step is performed by voice determination.

Figure 6B:
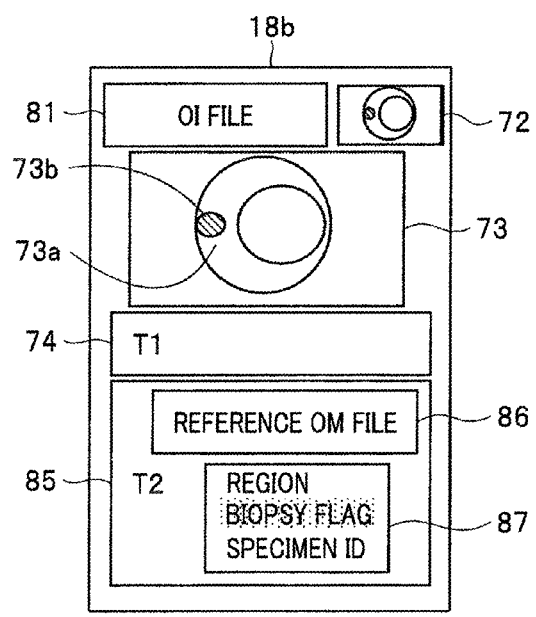
FIG. 6B is a diagram illustrating an example of screen display.

FIG. 6B illustrates an example of image display provided on the display screen 35*a* after editing work in step S30 or S40. When the clinician 51 has performed editing work of an image file, which is a source of an image that is being displayed, the control section 31 determines the edited image file as an OI file that is separate from an OM file. As illustrated in FIG. 6B, in the upper portion of the display screen 35*a*, a display 81 of "OI file" indicating that the image that is being displayed is one based on an image file modified by the information terminal 30 is provided. Also, in the lower portion of the display screen 35*a*, in addition to the display 74 based on related information, a display 85 of related information added by editing work using the information terminal 30 is added and provided. Here, although the display 74 provides only a display indicating the tag T1, the content of the display part is displayed by an operation to select the display part being performed.

In the display 85 based on related information newly added by an editing operation, a display of "T2" indicates that the display 85 is provided for related information designated by a tag T2 added by editing. Also, in the display 85 based on related information, a reference OM file display 86 indicating a file before editing is provided. The display 86 enables identification and reading of an image file before editing. Also, in a character display area 87 of the display 85, character strings indicating a region subjected to a biopsy, a biopsy flag and a specimen ID are provided as related information. The biopsy flag indicates that the image that is being displayed is an image at the time of cell or tissue acquisition. As the above step of providing specimen information, biopsy type information is determined, and thus, information on what type of detailed examination to be performed is also recorded. Also, the specimen ID indicates that the image that is being displayed is an image associated with a specimen identified by a specimen ID, that is, an image at the time of cell acquisition, which is identified by the specimen ID. Images can serve as search means representing a series of treatments.

Also, display on the display screen 35a in FIG. 5B indicates another display example according to the clinical application. On the right side of the display screen 35a, the selected picked-up image 56 is displayed, and on the left side of the display screen 35a, a related information display 60 related to the selected image is provided. In the related information display 60, the pieces of information designated by the tags T1 and T2 are included.

The control section 31 transmits the created OI file to the image management apparatus 20. The control section 21 of the image management apparatus 20 receives the image file (OI file) created by the information terminal 30 and provides the image file (OI file) to the recording section 23 to record the image file (OI file) in the recording section 23. The OI file recorded in the recording section 23 includes the related information indicating association between the specimen acquired by the specimen acquisition apparatus 10 and the image at the time of acquisition of the specimen. In the examination institution, accessing the image management apparatus 20 enables reading of the image file including the image at the time of acquisition of the specimen, using, e.g., the specimen ID provided to the sent specimen.

FIG. 5C illustrates an example in which the specimen examination apparatus 40 includes a chassis 40a in which the control section 41, etc., are housed, a microscope 40b included in the image input section 42 and a keyboard 43a included in the operation portion 43. In a front face of the chassis 40a, a display screen 48b of the display section 48 is disposed. The specimen examination apparatus 40 is operated by a laboratory technician 91.

Prior to an examination of a specimen, the laboratory technician 91 performs an input of information necessary for the examination. If the control section 41 determines in step S41 in FIG. 9 that no image is picked up by the image input section 42, an information acquisition operation is performed in step S48. For example, the laboratory technician 91 performs an operation to read a bar code label of a package in which the specimen is stored, using a bar code reader in the operation portion 43. Consequently, various types of information such as specimen ID, patient ID and biopsy flag relating to the specimen to be examined are acquired and recorded in the recording section 14 (step S49).

In step S50, the control section 41 determines whether or not a biopsy flag is included in the acquired information. Inclusion of biopsy flag information in the acquired information means that an image related to the specimen is recorded in the image management apparatus 20. In step S51, the control section 41 controls the communication section 45 to access the image management apparatus 20, and searches the image files to read the image file including the specimen ID provided to the specimen.

As described above, a treatment related to a living body is detected and an image file provided with specimen information according to the treatment is referred to when a detailed examination of a specimen is conducted, to easily review information in the file (e.g., the image itself, a used device, a used treatment instrument, a collection institution, a person who performed the collection, a patient ID, a time and a date of the collection, a collection position obtained from the use device), enabling enhancement in examination precision with little effort.

The laboratory technician 91 puts the non-illustrated specimen on a table 40d and conducts an examination of the specimen. Note that, in the examination of the specimen, predetermined processing such as staining and cutting of the specimen is performed. By operation performed by the laboratory technician 91, an image of the specimen is picked up and the picked-up image is supplied to the control section 41 via a cable 40c. The control section 41 provides a result of the image pickup to the display section 48 to display the result on the display section 48 and also provide the result to the recording section 44 to tentatively record the result in the recording section 44.

The laboratory technician 91 operates the microscope 40b as necessary. For example, in order to enable observation of a target region of the specimen, the laboratory technician 91 moves the stage 40d while reviewing an observation image on the display screen 48b of the display section 48. Upon detection of such operation (step S43), the control section 41 actuates the microscope 40b via the drive section 46 (step S44). In step S45, the control section 41 determines a change in position of the stage. Consequently, the control section 41 can figure out which region of the specimen is observed.

Upon obtaining an image suitable for an examination, the laboratory technician 91 performs an image pickup operation. If the control section 41 determines in step S46 that an image pickup operation is performed, the control section 41 performs shooting in step S47. On the display screen 48b in FIG. 5C, an image included in the image file read from the image management apparatus 20, that is, an image 93 at the time of cell acquisition is displayed. In acquisition of an image to be used for the examination of the specimen, the laboratory technician 91 can review the image at the time of acquisition of the specimen on the display screen 48b, and thus can acquire information that is extremely useful for the specimen examination. In addition, an image file (OI file) read from the image management apparatus 20 is provided with related information, and display of the related information is further useful for the specimen examination. As illustrated in FIG. 5C, on the display screen 48b, an image 94 based on an image acquired by the image specimen examination apparatus 40 (hereinafter referred to as "examination image") is displayed.

Also, the file creation section 41a can add various types of information as related information that can be designated by a tag T3, in response to an operation of the operation portion 43 such as the keyboard 43a by the laboratory technician 91. For example, the laboratory technician 91 adds, e.g., information relating to an examination result and an examination date. FIG. 5C indicates that on the display screen 48b, the tag T3 added via the specimen examination apparatus 40 is displayed in addition to the tags T1 and T2 added to the OI file read from the image management apparatus 20. The file creation section 41a creates an image file including the image acquired by the image input section 42 and the added related information (hereinafter referred to as "OS file") in addition to the image and the related information included in the image file read from the image management apparatus 20 (step S47).

The laboratory technician performs an operation to transmit the created OS file to the image management apparatus 20. The control section 41 makes the transition of the processing from steps S41 and S48 to step S52, and if the control section 41 determines that an image transmission operation is performed, the image file created in step S53 is transmitted to the image management apparatus 20 via the communication section 45.

The control section 21 of the image management apparatus 20 provides the image file (OS file) created by the specimen examination apparatus 40 to the recording section 23 to record the image file (OS file) in the recording section 23. The OS file recorded in the recording section 23 includes the image at the time of acquisition of the specimen, the image at the time of the examination of the specimen and the related information on the examination result.

The clinician 51 accesses the image management apparatus 20 to acquire the image file (OS file) including the information on the specimen examination result. In this case, an input of, e.g., an examination ID enables easy obtaining of the intended OS file. In this case, also, the clinician 51 activates the clinician application via the information terminal 30 to acquire the image file. In other words, in step S27 in FIG. 8, selection of a thumbnail enables selection of the intended OS file and display of the OS file on the display screen 35a.

Figure 6C:
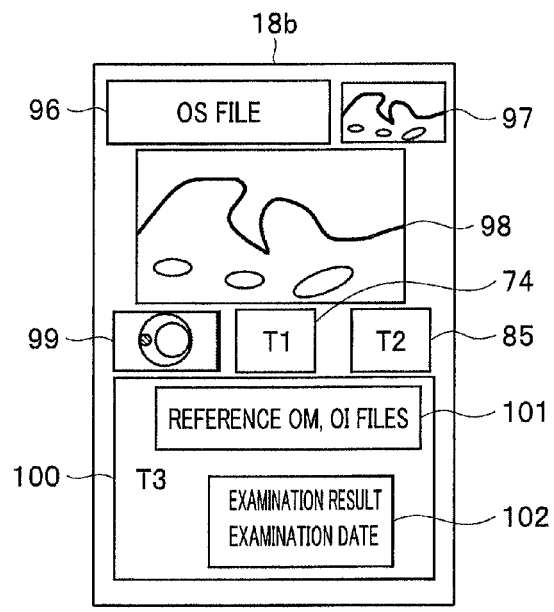
FIG. 6C is a diagram illustrating an example of screen display.

FIG. 6C illustrates an example of image display provided on the display screen 35a. As illustrated in FIG. 6C, in the upper portion of the display screen 35a, a display 96 of "OS file" indicating that the image that is being displayed is one based on the image file created by the specimen examination apparatus 40 is provided on the left side, and a thumbnail display 97 of the examination image is provided on the right side. Also, at a center of the display screen 35a, an examination image 98 is displayed. Also, on the left side of the center of the display screen 35a, a thumbnail display 99 of the image at the time of cell acquisition is provided and respective displays 74 and 85 designated by the tags T1 and T2 are provided at the center and on the right side. Also, in the lower portion of the display screen 35a, a display 100 based on the related information newly added by the editing operation via the specimen examination apparatus 40 is provided. "T3" indicates that the display 100 is provided for the related information designated by the tag T3, which has been added by editing. Also, in the display 100 based on the related information, a reference OM, OI file display 101 indicating a file before editing is provided. The display 101 enables identification and reading of an image file before editing. Also, in the display 100, in the character display area 102, character strings indicating an examination result of the specimen examination and a date of the examination are displayed as related information.

The clinician 51 can perform diagnosis for a patient with reference to the image illustrated in FIG. 6C. The clinician 51 inputs a result of the diagnosis as a finding input. In other words, in step S29, the control section 31 determines whether or not a finding input is provided, and if an input operation is performed by the clinician 51, in step S30, an operation to add information based on the input operation to the image file as related information is performed. As a result of the clinician 51 inputting the diagnosis result, the diagnosis result is added to the image file as related information. In this case, for example, the OS file including the examination result information may be edited to add the diagnosis result information to create a new OI file from the OS file. Also, a previous OI file obtained as a result of editing work via the information terminal 30 may further be edited, and also, an OM file obtained from the specimen acquisition apparatus 10 may be edited to add the diagnosis result information to create a new OI file from the OM file.

Figure 6D:
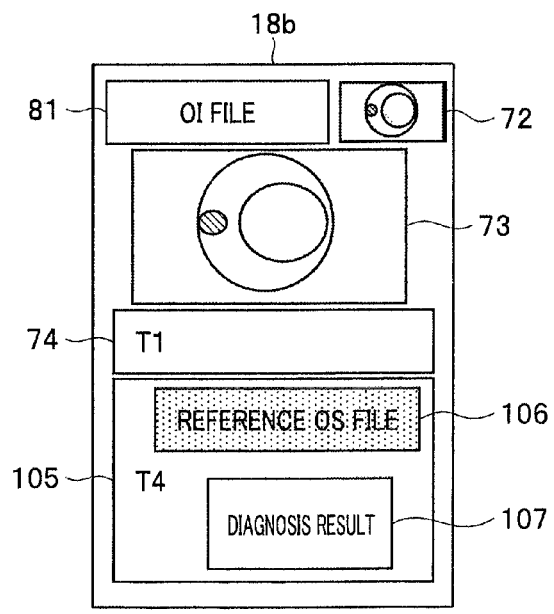
FIG. 6D is a diagram illustrating an example of screen display.

FIG. 6D illustrates an example of image display provided on the display screen 35a by the clinical application where the OM file illustrated in FIG. 6A is edited to create an image file in the editing work in step S30 or S40. If the clinician 51 performs editing work on an image file (OM file) that is a source of an image that is being displayed, the control section 31 makes the image file after the editing be an OI file that is different from the OM file. As illustrated in FIG. 6D, in the upper portion of the display screen 35a, a display 81 of "OI file" indicating that the image that is being displayed is one based on the image file modified by the information terminal 30 is provided. Also, in the lower portion of the display screen 35a, a display 105 based on the related information added by the editing work using the information terminal 30 is provided in addition to the display 74 based on related information. Here, although the display 74 provides indication of the tag T1 alone, if an operation to select the relevant display part is performed, the content of the tag T1 is displayed.

Note that the image file creation in step S40 may be the step of addition to a previously-existing image file, and in this case, the configuration is made so that data to be added later can be added to a previously-recorded image file. In other words, creation of an association area for association with a tissue examination result in a biopsy flag-provided image file enables addition to the association area without re-creation of the entire image file. The image file is preferably in a file format in which the image files before and after the addition are different from each other only in the added part.

Display of "T4" indicates that the display 105 based on the related information newly added by the editing operation is about related information designated by a tag T4, which has been added by editing. Also, in the display 105 based on the related information, a reference OS file display 106 indicating a file referred to before the editing is provided. The display 106 enables identification and reading of an image file (OS file) referred to at the time of the editing. Also, in a character display area 107 of the display 105, a character string indicating the diagnosis result inputted by the clinician 51 is displayed.

As described above, cells and images relating to the cells are associated with each other and the image files are managed in a centralized manner, enabling processing in another medical institution, etc., to be easily referred to in the respective medical institutions, etc., and thus, enables efficient processing in the respective medical institutions, etc. and facilitates management in the respective medical institutions, etc. In particular, processing in the respective medical institutions, etc., can be reviewed through an image, making it easy to understand the processing and providing contribution to safety enhancement.

Figure 8:
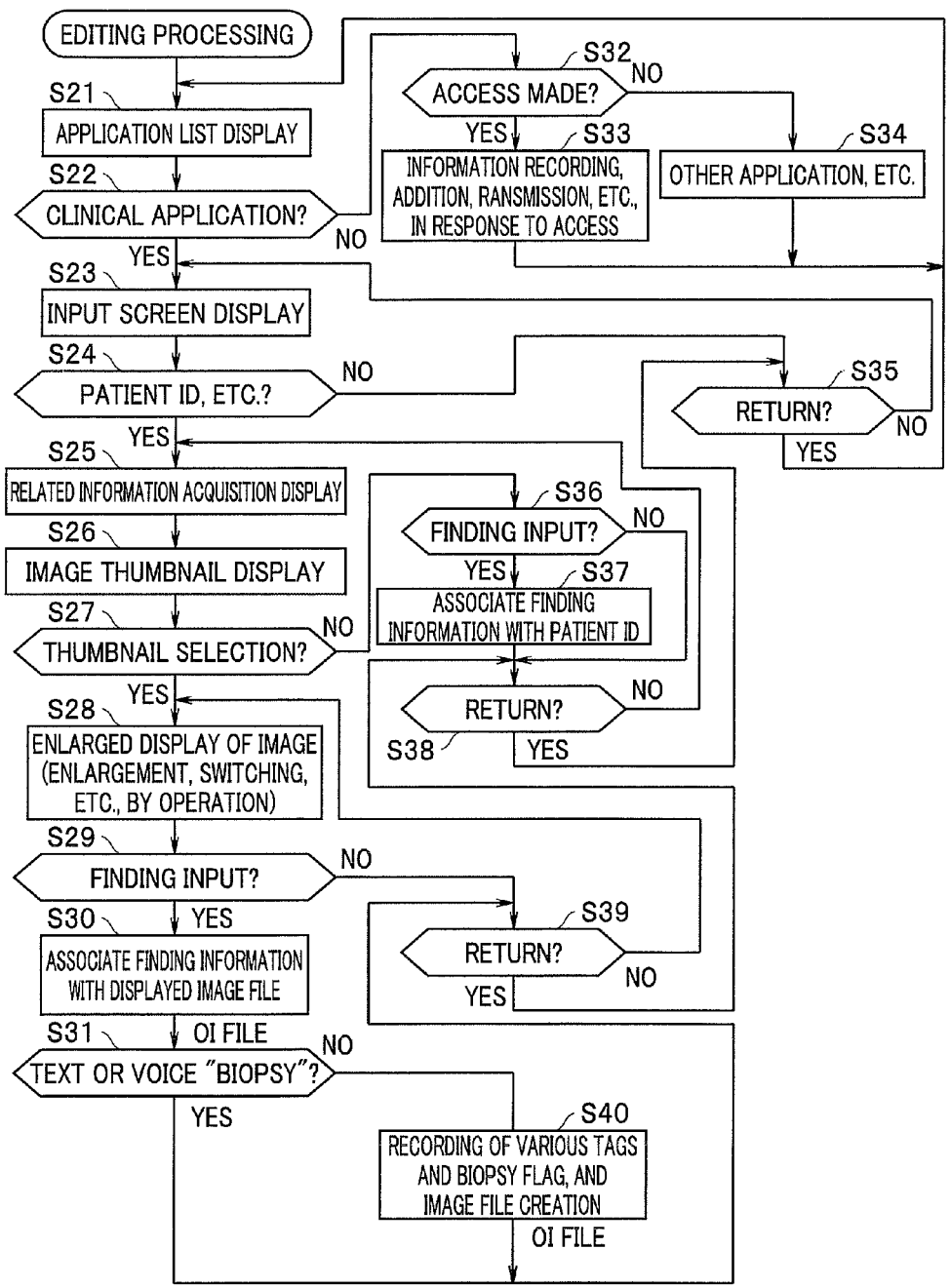
FIG. 8 is a flowchart for describing operation in an embodiment.
Figure 9:
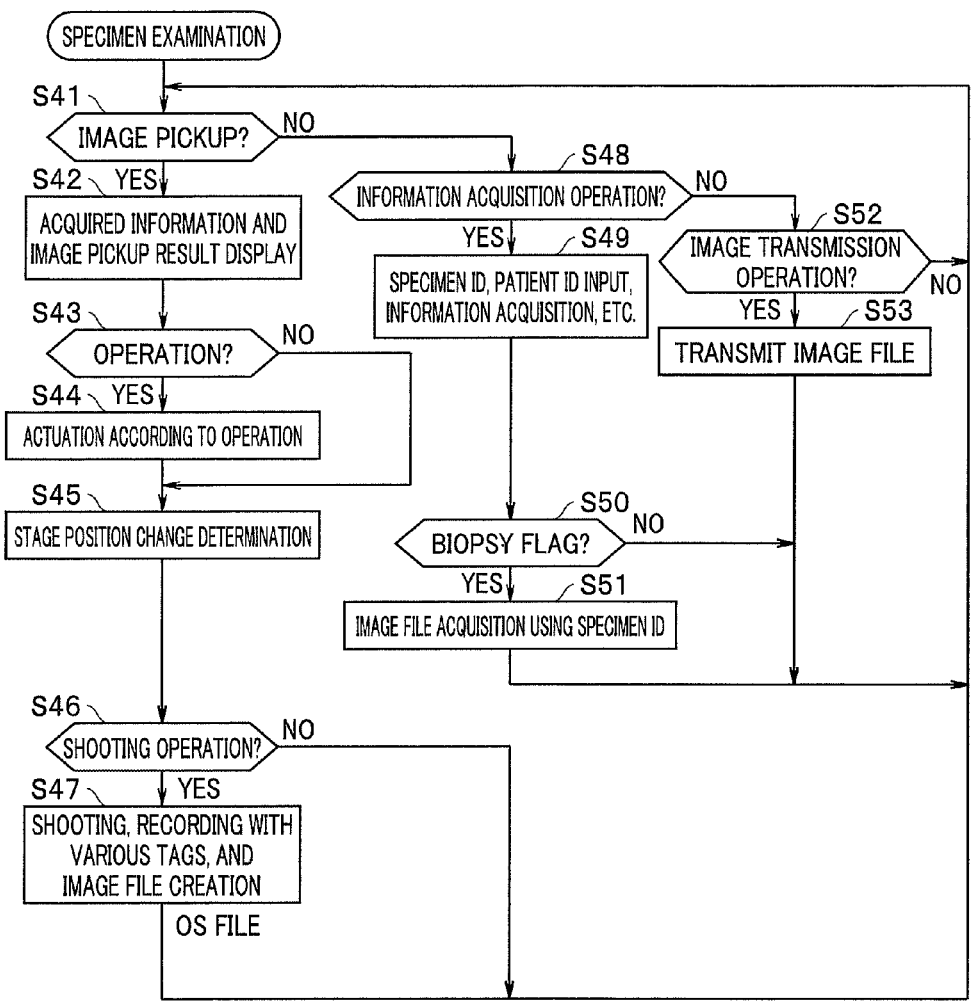
FIG. 9 is a flowchart for describing operation in an embodiment.

Here, in step S33 in FIG. 8, the control section 21 of the image management apparatus 20 performs processing according to access from each bio-related apparatus, but all pieces of information on each patient can be centrally managed in the image management apparatus 20. For example, it is possible that the operation determination section 24 receives information from a patient registration card reader via the communication section 22 and provides a result of analysis of the information to the control section 21. The control section 21 can perform management on the relevant patient based on the information read from the patient registration card.

Figure 10:
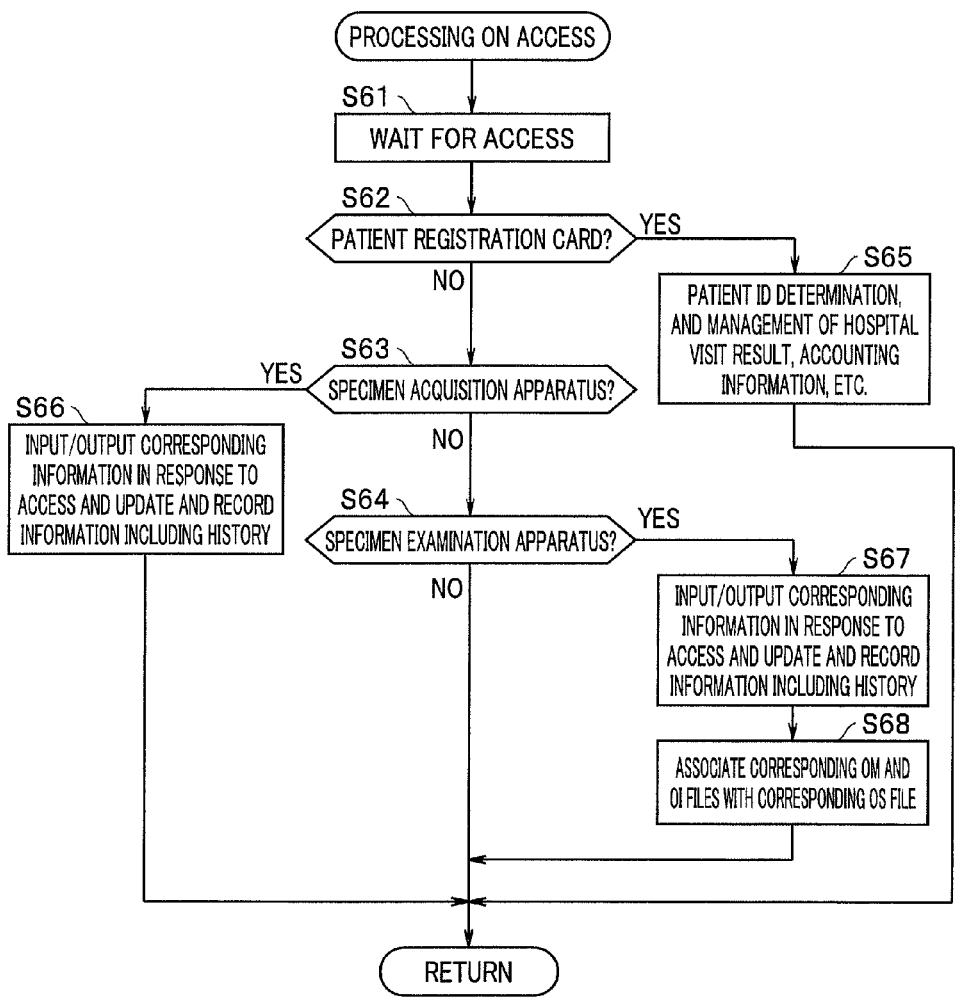
FIG. 10 is a flowchart for describing operation in an embodiment.

FIG. 10 illustrates processing performed instead of the processing in step S33. The control section 21 enters an access wait state in step S61. Upon access being made, in steps S62 to S64, the control section 21 determines whether the access is made by reading of a patient registration card, is made from the specimen acquisition (tissue collection) apparatus 10 or is made from the specimen examination apparatus 40. If the access is made by reading of a patient registration card, in step S65, the control section 21 determines an patient ID and updates and manages a result of the hospital visit, accounting information, etc.

Also, if the access is made from the specimen acquisition (tissue collection) apparatus 10, the control section 21 inputs/outputs corresponding information in response to the access, and updates and records the information including an access history (step S66). Also, if the access is made from the specimen examination apparatus 40, the control section 21 inputs/outputs corresponding information in response to the access and updates and records the information including the access history (step S67). Also, the control section 21 associates corresponding OM, OI and OS files (step S68).

As described above, in the present embodiment, a tissue or a cell and an image related to the tissue or the cell are recorded in association with each other and are managed in a centralized manner, enabling images related to a history, an origin and processing for a tissue or a cell from, e.g., a living body to be easily reviewed in a plurality of medical institutions, etc. Consequently, it is possible to assist safe and reliable processing in the respective medical institutions, etc. Also, the image files managed in a centralized manner include information obtained via bio-related apparatuses in the respective medical institutions and information such as results of examinations and results of diagnoses by clinicians, laboratory technicians, etc. and thus are extremely useful.

Also, in a specimen acquisition (tissue collection) apparatus, upon collection of a tissue or acquisition of a specimen, a biopsy flag indicating that the relevant image is an image at the time of cell acquisition is automatically added to an image file, enabling determination of whether or not the image is one at the time of specimen acquisition without a surgeon performing a troublesome operation.

Although the above embodiment has been described in terms of an example in which a biopsy is conducted in a hospital and an acquired specimen is examined in an examination institution, a known encryption technique and/or an authentication function are added or linked as necessary, ensuring reliability through sharing of mutually helpful information among medical institutions etc., that deal with tissues and cells and images relating to the tissues and the cells.

For example, the above embodiment can be applied to a case where tissues and cells and images relating to the tissues and the cells in regenerative medicine, etc. are dealt with. For example, while case examples in which iPS cells are infused to the inside of the body of an animal to produce a human organ and the organ is implanted in a human in a hospital have come to fruition in the regenerative medicine in research institutions, etc., organizing origins and histories of collected objects is increasingly important, and it is indisputable that the technique of the present invention in which images relating to tissues and cells are acquired in each step and managed in a centralized manner together with related information as image files is an application effective for the regenerative medicine. In other words, in this case, it is only necessary to employ a cell processing apparatus using, e.g., a microscope that can process a cell instead of a specimen acquisition apparatus and a cell processing apparatus such as an endoscope for cell implant instead of a specimen examination apparatus. Furthermore, the range of application of the technique of the present invention can be expanded also to antibody production, pharmaceutical production, etc. In each step of processing in a research institution, a hospital or the like, processing performed in another medical institution or the like can be reviewed and the content of the processing performed in the relevant institution can be added together with images as related information. In the respective medical institutions, etc., image files managed in a centralized manner are reviewed, enabling obtainment of extremely useful information. Not only the medical institutions, but also universities and laboratories may utilize such system. Also, where a particular cell or tissue is studied, such cell or tissue is not necessarily collected from a living body, and the parts each referred to as "living body" above may be referred to as, e.g., "origin of a collected object".

In the study of, e.g., the regenerative medicine, "clinical trial data collection and reporting" is important. Image files created in the present embodiment can be used also for, e.g., a history regarding whether or not a clinical trial using a collected specimen is correctly conducted. For example, writing a necessary report by a doctor or in a research institution or the like in association with an image file created in the present embodiment enables centralized data management of troublesome treatments in a clinical trial and thus is useful for, e.g., tracking of the clinical trial.

Note that, although the above embodiment has been described taking an endoscope as an example of a device for shooting, any shooting device may be employed as long as such shooting device can shoot an image of a manner of collection or processing of an object to be observed such as a part of an organ, a tissue, a cell, a foreign object, etc., collected from, e.g., a living body. Also, although an example of an endoscope with biopsy forceps inserted have been described as a specimen acquisition apparatus, image pickup and a biopsy may be performed by different devices, respectively. Any of the apparatuses can organize various types of information and data according to a particular program or by an electric circuit to create an image file.

The present invention is not limited to the above-described embodiments as it is, and in the practical phase, can be embodied with components modified without departing from the spirit of the invention. Also, each of various aspects of the invention can be formed by an arbitrary combination of a plurality of components disclosed in the above embodiment. For example, some components may be deleted from all the components indicated in an embodiment.

Note that, even though the operation flows in the claims, the specification and the drawings are described using "first, "next", etc., for sake of convenience, this does not means that it is essential to perform the operation flows in such order. Also, it is not disputable that parts of the respective steps included in the operation flows, the parts not affecting the essence of the invention, can arbitrarily be omitted.

Note that, from among the techniques described here, mainly the controls described with reference to the flowcharts can often be set by programs, which may be recorded in a recording medium or a recording section. As a method of recording onto the recording medium or the recording section, the recording may be performed at the time of product shipment, a distributed recording medium may be used or the recording may be performed by downloading via the Internet.

[Notes]

[Note 1]

A medical system including:

an image management apparatus configured to hold an image file of an image relating to a cell, related information indicating a relation between the cell and the image being added to the image file; and a bio-related apparatus configured to be capable of accessing the image management apparatus, the bio-related apparatus including a control section configured to read the image file and provide display based on the image and the related information.

[Note 2]

The medical system according to note 1, wherein the bio-related apparatus includes an information terminal configured to read the image file and edit the image file.

[Note 3]

The medical system according to note 1 or 2, wherein the bio-related apparatus includes at least one of the cell acquisition apparatus configured to acquire the cell and the cell examination apparatus configured to examine the cell.

[Note 4]

The medical system according to note 3, wherein the cell acquisition apparatus includes an endoscope configured to acquire the cell.

[Note 5]

The medical system according to note 3, wherein the cell acquisition apparatus includes an image pickup section, and acquires an image at a time of acquisition of the cell, the image being picked up by the image pickup section at the time of acquisition of the cell, as the image relating to the cell.

[Note 6]

The medical system according to note 5, wherein the cell acquisition apparatus determines the time of acquisition of the cell by determination of operation of an instrument used for acquisition of the cell or image analysis of an image including the cell.

[Note 7]

The medical system according to note 5, wherein the cell acquisition apparatus adds information identifying the image relating to the cell at the time of acquisition of the cell to the image file.

[Note 8]

The medical system according to note 2, wherein the information terminal adds information identifying the cell to the image file as the related information.

[Note 9]

The medical system according to note 3, wherein the cell examination terminal is capable of editing the image file.

[Note 10]

The medical system according to note 3, wherein the cell examination terminal includes an image pickup section, and acquires an image at a time of examination of the cell, the image being picked up by the image pickup section at the time of examination of the cell, as the image relating to the cell.

[Note 11]

A medical image display method including:

a procedure for causing an image management apparatus to hold an image file of an image relating to a cell, related information indicating a relation between the cell and the image being added to the image file; and a procedure for causing a bio-related apparatus capable of accessing the image management apparatus to read the image file and provide display based on the image and the related information.

[Note 12]

A medium with a medical image display program recorded, the medical image display program causing a computer to perform a procedure for accessing an image management apparatus in which an image file of an image relating to a cell, related information indicating a relation between the cell and the image being added to the image file, is held and a procedure for reading the image file and providing display based on the image and the related information.

What is claimed is:

1. An image file creation method that enhances reliability of a surgical treatment, the method comprising:

receiving a first image of a living body from an imager, wherein the first image is acquired by the imager prior to the surgical treatment;

determining a first orientation of the imager when the first image was acquired based on first data received from one or more sensors of the imager during the surgical treatment;

identifying a feature within the first image;

receiving a second image of the living body from the imager determining a second orientation of the imager when the second image was acquired based on second data received from the one or more sensors of the imager during the surgical treatment;

detecting a change in the feature within the second image; and on a condition that the first orientation and the second orientation are equivalent;

detecting that the surgical treatment has been performed based on the change in the feature detected, and storing an image file that includes the first image and the second image to enhance the reliability of the surgical treatment.

2. The image file creation method according to claim 1, wherein the feature within the first image is identified by searching a database of features for a treatment instrument that is included in the first image or a living body tissue that is included in the first image.

3. The image file creation method according to claim 2, further comprising:

acquiring biopsy type information by determining a type of the biopsy, wherein the image file further includes the biopsy type information.

4. The image file creation method according to claim 1, further comprising acquiring biopsy type information by determining a type of the biopsy, wherein the image file further includes the biopsy type information.

5. The image file creation method according to claim 1, wherein the image file further includes an association area enabling association with a tissue examination result.

6. The image file creation method according to claim 1, wherein the imager is an endoscope.

7. The image file creation method according to claim 1, wherein the imager is a wearable camera worn by an individual performing the surgical treatment.

8. A non-transitory computer readable storage medium with an image file creation program recorded, the image file creation program that enhances reliability of a surgical treatment, wherein the image file creation program when executed by a computer causes the computer to:
- receive a first image of a living body from an imager, wherein the first image is acquired by the imager prior to the surgical treatment;
- determine a first orientation of the imager when the first image was acquired based on first data received from one or more sensors of the imager during the surgical treatment;
- identify a feature within the first image;
- receive a second image of the living body from the imager
- determine a second orientation of the imager when the second image was acquired based on second data received from the one or more sensors of the imager during the surgical treatment;
- detect a change in the feature within the second image; and
- on a condition that the first orientation and the second orientation are equivalent, the image file creation program causes the computer to:
  - detect that the surgical treatment has been performed based on the change in the feature detected, and
  - store an image file that includes the first image and the second image to enhance the reliability of the surgical treatment.

9. The non-transitory computer readable storage medium according to claim 8, wherein the imager is an endoscope.

10. The non-transitory computer readable storage medium according to claim 8, wherein the imager is a wearable camera worn by an individual performing the surgical treatment.

11. An image file creation apparatus that enhances reliability of a surgical treatment, the apparatus comprising:
- a communication interface that is communicatively coupled to an imager, wherein the imager includes one or more sensors that measure an orientation of the imager;
- a memory; and
- a processor that is communicatively coupled to the communication interface and the memory, wherein the processor:
- receives, using the communication interface, a first image of a living body from the imager, wherein the first image is acquired by the imager prior to the surgical treatment;
- determines, using the communication interface, a first orientation of the imager when the first image was acquired based on first data received from the one or more sensors of the imager during the surgical treatment;
- identifies a feature within the first image;
- receives, using the communication interface, a second image of the living body from the imager;
- determines a second orientation of the imager when the second image was acquired based on second data received from the one or more sensors of the imager;
- detects a change in the feature within the second image; and
- on a condition that the first orientation and the second orientation are equivalent;
  - detects the surgical treatment has been performed based on the change in the feature detected, and
  - stores an image file that includes the first image and the second image in the memory to enhance the reliability of the surgical treatment.

12. The image file creation apparatus according to claim 11, wherein the imager is an endoscope.

13. The image file creation apparatus according to claim 11, wherein the imager is a wearable camera worn by an individual performing the surgical treatment.

* * * * *